(12) United States Patent
Thomas

(10) Patent No.: US 12,364,744 B2
(45) Date of Patent: Jul. 22, 2025

(54) METHODS AND COMPOSITIONS FOR THE DIAGNOSIS, PROPHYLAXIS AND TREATMENT OF LYME DISEASE

(71) Applicant: Lankenau Institute for Medical Research, Wynnewood, PA (US)

(72) Inventor: Sunil Thomas, Philadelphia, PA (US)

(73) Assignee: Lankenau Institute for Medical Research, Wynnewood, PA (US)

( * ) Notice: Subject to any disclaimer, the term of this patent is extended or adjusted under 35 U.S.C. 154(b) by 0 days.

(21) Appl. No.: 17/534,970

(22) Filed: Nov. 24, 2021

(65) Prior Publication Data

US 2022/0160856 A1    May 26, 2022

Related U.S. Application Data

(60) Provisional application No. 63/118,101, filed on Nov. 25, 2020.

(51) Int. Cl.
  *A61K 39/02*  (2006.01)
  *A61K 39/00*  (2006.01)
  (Continued)

(52) U.S. Cl.
  CPC .......... *A61K 39/0225* (2013.01); *A61P 31/04* (2018.01); *G01N 33/6893* (2013.01);
  (Continued)

(58) Field of Classification Search
  CPC .............. A61P 31/04; A61K 39/0225; A61K 2039/521; A61K 2039/53; A61K 2039/54;
  (Continued)

(56) References Cited

U.S. PATENT DOCUMENTS

| | | |
|---|---|---|
| 5,656,451 A | 8/1997 | Flavell et al. |
| 5,807,685 A | 9/1998 | Flavell et al. |

(Continued)

FOREIGN PATENT DOCUMENTS

| | | | | |
|---|---|---|---|---|
| WO | WO1995012676 | * | 5/1995 | ............. C07K 14/20 |
| WO | WO-2013067448 A2 | * | 5/2013 | ........... C07K 14/195 |
| WO | WO-2016193370 A1 | * | 12/2016 | ........... A61K 35/744 |

OTHER PUBLICATIONS

Steere AC, et al. (Dec. 2016) Lyme borreliosis. Nat Rev Dis Primers 2:16090.

(Continued)

*Primary Examiner* — Jana A Hines
(74) *Attorney, Agent, or Firm* — Howson & Howson, LLP; Colleen M. Schaller; Richard F. Kane

(57) ABSTRACT

Reagents that include certain identified peptides derived from *B. burgdorferi* proteins, or nucleic acid sequences encoding same are useful in the diagnosis of Lyme borreliosis (Lyme Disease) in infected subject are disclosed herein. Such reagents can also include nucleic acid sequences encoding the peptides. Pharmaceutical compositions useful for the treatment or prophylaxis of *B. burgdorferi* infection include certain peptides derived from *B. burgdorferi* proteins, or nucleic acid sequences encoding same. Methods of treating or preventing Lyme borreliosis (Lyme Disease) include administering effective amount of such pharmaceutical compositions. An antibody independent prophylactic pharmaceutical composition comprises a sonicate of *B. burgdorferi* bacterium; and methods of treating or preventing Lyme borreliosis include administering effective amounts of that sonicate composition are also disclosed herein.

15 Claims, 5 Drawing Sheets

Specification includes a Sequence Listing.

(51) Int. Cl.
*A61P 31/04* (2006.01)
*G01N 33/68* (2006.01)

(52) U.S. Cl.
CPC .... *A61K 2039/521* (2013.01); *A61K 2039/53* (2013.01); *G01N 2333/20* (2013.01); *G01N 2800/26* (2013.01)

(58) Field of Classification Search
CPC ... A61K 2039/55566; G01N 33/56911; G01N 33/6893; G01N 33/00; G01N 31/00; G01N 33/48; G01N 33/50; G01N 33/68; G01N 33/6896; G01N 2333/20; G01N 2800/26

See application file for complete search history.

(56) References Cited

U.S. PATENT DOCUMENTS

| | | | |
|---|---|---|---|
| 5,853,987 | A | 12/1998 | Guo et al. |
| 6,228,835 | B1 | 5/2001 | Guo et al. |
| 6,248,517 | B1 | 6/2001 | Guo et al. |
| 6,312,907 | B1 | 11/2001 | Guo et al. |
| 6,716,591 | B1 | 4/2004 | Flavell et al. |
| 9,310,367 | B2 | 4/2016 | Burbelo et al. |
| 9,844,679 | B2 | 12/2017 | Nayfach-Battilana |
| 2004/0071703 | A1 | 4/2004 | Brown et al. |
| 2012/0142023 | A1* | 6/2012 | Ascoli .............. G01N 33/56911 435/7.1 |
| 2014/0274926 | A1* | 9/2014 | Jin et al. .............. C07D 471/04 544/127 |
| 2016/0106825 | A1 | 4/2016 | Thomas et al. |
| 2016/0123978 | A1 | 5/2016 | De Leão E Flores et al. |
| 2020/0255889 | A1 | 8/2020 | Tokarz et al. |

OTHER PUBLICATIONS

Shapiro ED (Dec. 2014) Clinical practice. Lyme disease. N Engl J Med 370:1724-1731.
Kullberg BJ, et al. (May 2020) Lyme borreliosis: diagnosis and management. BMJ 369:m1041.
Roberts ED, et al. (Mar. 1998) Pathogenesis of Lyme neuroborreliosis in the rhesus monkey: the early disseminated and chronic phases of disease in the peripheral nervous system. J Infect Dis 178:722-732.
Logigian EL, et al. (Nov. 1990) Chronic neurologic manifestations of Lyme disease. N Engl J Med 323:1438-1444.
Bratton RL, et al. (May 2008) Diagnosis and treatment of Lyme disease. Mayo Clin Proc 83: 566-571.
Burgdorfer W, et al. (Jun. 1982) Lyme disease—a tick-borne spirochetosis? Science 216:1317-1319.
Elbaum-Garfinkle S (Jun. 2011) Close to home: a history of Yale and Lyme disease. Yale J Biol Med 84:103-108.
Kenedy MR, et al. (Apr. 2012) The role of *Borrelia burgdorferi* outer surface proteins. FEMS Immunol Med Microbiol 66:1-19.
Fraser C, Casjens S, Huang W et al.(Dec. 1997) Genomic sequence of a Lyme disease spirochaete, *Borrelia burgdorferi*. Nature 390: 580-586.
Iliopoulou BP, et al. (Dec. 2009) HLA-DR alleles determine responsiveness to Borrelia burgdorferi antigens in a mouse model of self-perpetuating arthritis. Arthritis Rheum 60: 3831-3840.
Barbour AG, et al. (Feb. 1996) Identification of an uncultivable *Borrelia* species in the hard tick *Amblyomma americanum*: possible agent of a Lyme disease-like illness. J Infect Dis 173: 403-409.
Sánchez RST, et al. (Apr. 2020) Rodents as potential reservoirs for *Borrelia* spp. in northern Chile. Rev Bras Parasitol Vet 29(2):e000120.
Caimano MJ et al. (Aug. 2019) The RpoS Gatekeeper in Borrelia burgdorferi: An Invariant Regulatory Scheme That Promotes Spirochete Persistence in Reservoir Hosts and Niche Diversity. Front. Microbiol. 10:1923. doi: 10.3389/fmicb.2019.01923.
Werner, Ashley. Outer surface protein (Osp) F subfamily antibody responses during Lyme disease. Diss. Dec. 2018.
Herding, E.J. Prospects for development of an effective Lyme disease vaccine. MS in Clinical Microbiology, May 2016, 40pp. (S. Callister).
Brock, Christina Marie (Aug. 2017). Development of a Novel, Peptide-based Vaccine for Lyme Disease. Doctoral dissertation, Texas A & M University.
Nerina Jusufovic. Re-evaluation of CspZ, a complement regulator-acquiring surface protein of the Lyme disease spirochete Borrelia burgdorferi, as a potential vaccine target in a canine host.MS in Biology, Dec. 2017.
Jutras, B.L, et al. (Jul. 2019), The Lyme disease spirochete's BpuR DNA/RNA-binding protein is differentially expressed during the mammal-tick infectious cycle, which affects translation of the SodA superoxide dismutase. Mol Microbiol, 112: 973-991.
Casjens, S.R., Di, L., Akther, S. et al. Primordial origin and diversification of plasmids in Lyme disease agent bacteria. BMC Genomics 19, 218 (Mar. 2018).
Shrestha B, et al. (Feb. 2017). Outer membrane proteins BB0405 and BB0406 are immunogenic, but only BB0405 is required for Borrelia burgdorferi infection. Infect Immun 85:e00803-16.
Tkáčvá Z et al. Identification of the proteins of Borrelia garinii interacting with human brain microvascular endothelial cells. Ticks Tick Borne Dis. Jul. 2020;11(4) 101451.
Bolivar, Patricia D. Health Promoting Behaviors of Young Adults with Chronic Lyme Disease. Diss. Walden University, Feb. 2018.
Godallier, Morgane. "Maladie de Lyme chez le chien: pathogénie, diagnostic, et prévention." (Jul. 2020).
Kao, Wei-Chien Andrew. Identification and Characterization of Candidate Treponema pallidum Vascular Adhesins by Heterologous Expression in the Lyme Disease Pathogen. Diss. University of Toronto (Canada), Nov. 2016.
Hart T, et al. (May 2018) Polymorphic factor H-binding activity of CspA protects Lyme borreliae from the host complement in feeding ticks to facilitate tick-to-host transmission. PLoS Pathog 14(5): e1007106. https://doi.org/10.1371/journal.ppat. 1007106.
Graham DE, et al. (Nov. 2020). The BB0345 hypothetical protein of Borrelia burgdorferi is essential for mammalian infection. Infect Immun 88:e00472-20.
Szewczyk, J., and J-F. Collet. "The journey of lipoproteins through the cell: one birthplace, multiple destinations." Advances in Microbial Physiology 69 (Aug. 2016): 1-50.
Brown, Gemma. Characterisation and structural studies of a superoxide dismutase and OmpA-like proteins from Borrelia burgdorferi sensu lato. Diss. University of Huddersfield, (Jul. 2016).
Franklin, Freddy, et al. "Evaluation of Salmonella Typhi antigen YncE alongside HlyE for the detection of typhoid fever and its carriers." Medical microbiology and immunology 209.5 (Apr. 2020): 593-601.
Vechtova, P., Sterbova, J., Sterba, J. et al. A bite so sweet: the glycobiology interface of tick-host-pathogen interactions. Parasites Vectors 11, 594 (Nov. 2018).

* cited by examiner

FIG. 4

METHODS AND COMPOSITIONS FOR THE DIAGNOSIS, PROPHYLAXIS AND TREATMENT OF LYME DISEASE

CROSS-REFERENCE TO RELATED APPLICATIONS

This application claims priority to U.S. Provisional application 63/118,101 filed Nov. 25, 2020, the entire contents being incorporated herein by reference as though set forth in full.

INCORPORATION-BY-REFERENCE OF MATERIAL SUBMITTED IN ELECTRONIC FORM

Incorporated herein by reference in its entirety is the sequence listing submitted via EFS-Web as a text file named SEQLIST.txt, created Nov. 22, 2021, and having a size of 26,882 bytes.

FIELD OF THE INVENTION

This invention relates to reagents that include certain identified peptides derived from *B. burgdorferi* proteins, or nucleic acid sequences encoding same that are useful in the diagnosis, treatment, and prevention of Lyme borreliosis (Lyme Disease) in an infected subject.

BACKGROUND OF THE INVENTION

Ticks are responsible for transmission of Lyme disease, ehrlichiosis, rickettsiosis, anaplasmosis, etc. Most of the diseases transmitted by ticks are neglected diseases as they affect only hundreds of people in the rural areas. However, such diseases have the potential to cause widespread infection under suitable conditions and are often misdiagnosed leading to fatalities. Lyme disease has become recognized as the most prevalent arthropod-borne infection in the United States (Centers for Disease Control, 1996). The incidence of Lyme disease is increasing over the years. There are no commercial vaccines available that effectively provide protection against *Borrelia burgdorferi*, the bacteria responsible for Lyme disease.

The genus *Borrelia* is a member of the family Spirochaetacaea (spirochetes). The incidence of Lyme disease in the United States has been increasing since national surveillance with the use of a standardized case definition was instituted in 1991. There is no way of knowing exactly how many people get Lyme disease. A recently released estimate based on insurance records suggests that each year approximately 76,000 Americans are diagnosed and treated for Lyme disease. This number is likely an over-estimate of actual infections because patients are sometimes treated presumptively in medical practice. Regardless, this number indicates a large burden on the health care system and the need for more effective prevention measures.

The great majority of cases occur in north-eastern United States, with additional foci in northern midwestern states (Wisconsin and Minnesota). Lyme disease also occurs in the Pacific coastal regions of Oregon and northern California. Although the geographic range of Lyme disease remains limited, it has been expanding, primarily due to changes in climate. The incidence of Lyme disease is highest among children 5 to 14 years of age and middle-aged adults (40 to 50 years of age), and it is slightly more common among males than among females.

The most common sign of Lyme disease is erythema migrans. Erythema migrans usually begins as a small erythematous papule or macule that appears at the site of the tick bite 1 to 2 weeks later and subsequently enlarges. The skin lesion is frequently accompanied by influenza-like symptoms, such as malaise and fatigue, headache, arthralgias, myalgias, fever, or regional lymphadenopathy, and these symptoms may be the presenting manifestation of the illness. The spread of *B. burgdorferi* within the nervous system has been demonstrated in nonhuman primates. In up to 5 percent of untreated patients, *B. burgdorferi* may cause chronic neuroborreliosis, sometimes after long periods of latent infection.

Clearly, effective methods for diagnosing, treating, and preventing Lyme Disease are needed.

SUMMARY OF THE INVENTION

In one aspect, a reagent useful for the diagnosis of Lyme borreliosis in a subject comprises a peptide of SEQ ID NO: 10, 11, 12, 13, 14, 15, 16, 17 or 18. In another aspect, the reagent comprises a peptide having at least 90% identity to a peptide of any of SEQ ID NO: 10 through 18. In another aspect, the reagent comprises a peptide variant differing in one or more conservative amino acids to a peptide of any one of SEQ ID NO: 10 through 18. In another embodiment, the reagent comprises a peptide variant differing in one or more naturally occurring amino acids from a peptide of SEQ ID NO: 10 through 18, based upon the strain of *B. burgdorferi* from which the peptide sequence is derived.

In another aspect, a reagent comprises a mixture of multiple of the peptides identified herein.

In another aspect, a reagent useful for the diagnosis of Lyme borreliosis in a subject comprises a nucleic acid sequence encoding any of the peptides identified herein.

In another aspect, a reagent comprises a mixture of the nucleic acid sequences encoding multiple peptides identified herein.

In one aspect, a method for diagnosing Lyme borreliosis includes contacting a biological sample from a subject with one or more of the reagents described herein.

In yet another aspect, a pharmaceutical composition for the treatment, inhibition, or prophylaxis of Lyme borreliosis comprises a peptide of SEQ ID NO: 10, 11, 12, 13, 14, 15, 16, 17 or 18 and a pharmaceutically acceptable carrier, excipient, or adjuvant. In another aspect, the composition comprises a peptide having at least 90% identity to a peptide of any of SEQ ID NO: 10 through 18 and a pharmaceutically acceptable carrier, excipient, or adjuvant. In another aspect, the composition comprises a peptide variant differing in one or more conservative amino acids to a peptide of any one of SEQ ID NO: 10 through 18 and a pharmaceutically acceptable carrier, excipient, or adjuvant. In another embodiment, the composition comprises a peptide variant differing in one or more naturally occurring amino acids from a peptide of SEQ ID NO: 10 through 18, based upon the strain of *B. burgdorferi* from which the peptide sequence is derived and a pharmaceutically acceptable carrier, excipient, or adjuvant. In still another embodiment, this composition contains two or more of these peptides in admixture and a pharmaceutically acceptable carrier, excipient, or adjuvant.

In another aspect, a pharmaceutical composition for the treatment, inhibition, or prophylaxis of Lyme borreliosis comprises a nucleic acid sequence encoding any of the peptides identified herein and a pharmaceutically acceptable carrier, excipient, or adjuvant. In still another embodiment, this composition further contains a single nucleic acid sequence encoding multiple different peptides described herein, or a mixture of different nucleic acid sequences, each sequence encoding a different peptide described herein.

Yet another aspect provides a method of treating, preventing, inhibiting, or retarding infection by *B. burgdorferi* comprising administering to a subject in need thereof an effective amount of a pharmaceutical composition as described herein.

In another aspect, a pharmaceutical composition for the treatment, retarding or prophylaxis of Lyme borreliosis comprises a sonicate of *Borrelia burgdorferi*.

In yet another aspect, a method of treating, preventing, or retarding infection comprises administering to a subject in need thereof, an effective amount of a pharmaceutical composition comprising a sonicate of *Borrelia burgdorferi*, wherein the sonicate elicits an antibody-independent protective immune response.

Still other aspects and advantages of these compositions and methods are described further in the following detailed description of the preferred embodiments thereof.

BRIEF DESCRIPTION OF THE DRAWINGS

FIG. 4 is a graph showing bacterial load. C3H/HeN mice were immunized at day 0 and 14 and were infected at 4 weeks post-priming with $10^5$ *Borrelia* cells per mouse. Two weeks post-infection mice were euthanized, and tissues were collected to evaluate bacterial burden. The tissues are identified on the X axis and the various peptides and controls are identified below each bar.

DETAILED DESCRIPTION

Figure 1A:
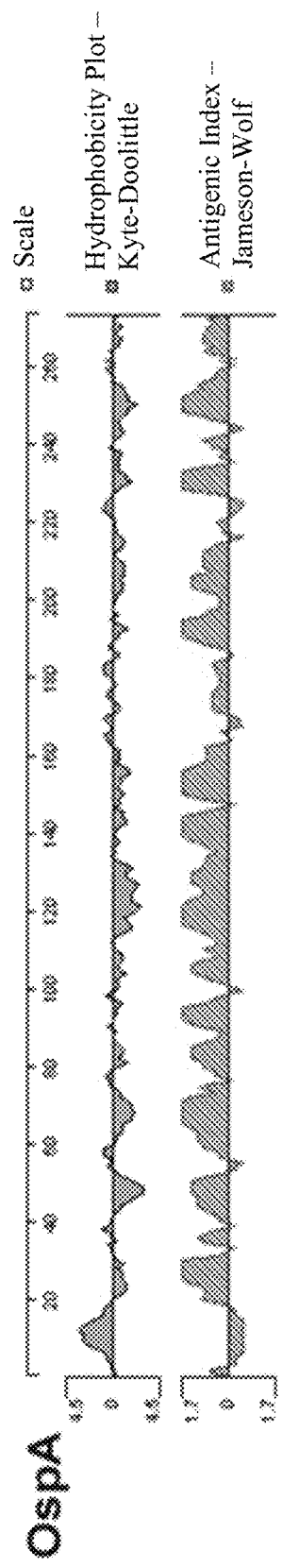
FIG. 1A-1D are hydrophobic plots of the antigens of *Borrelia*, OspA, OspC, P100 and VlsE, respectively. The epitopes are selected based on hydrophilicity.
Figure 1B:
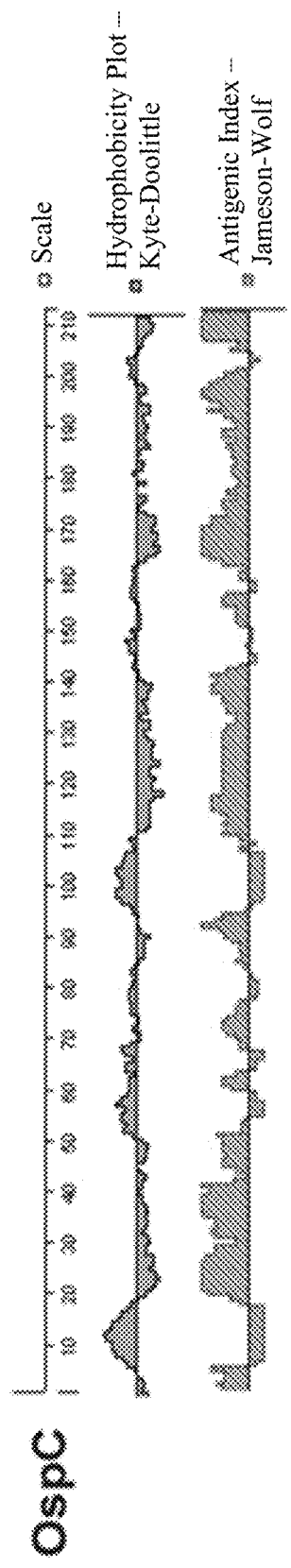
Figure 1C:
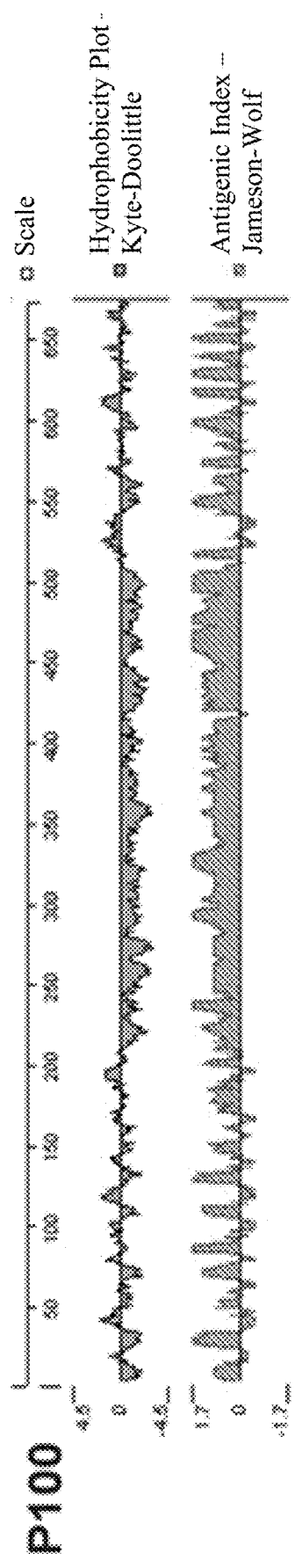
Figure 1D:
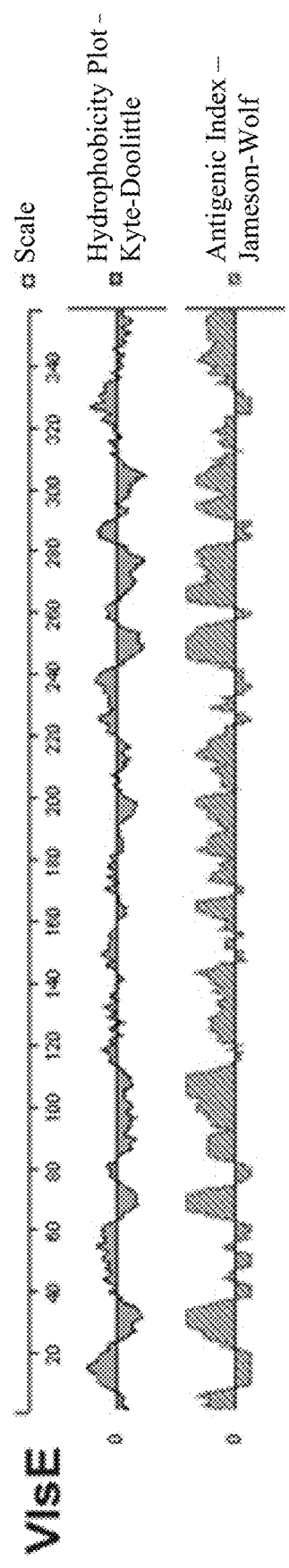

In response to the continuing need in the art that exists for new and effective tools and methods for the diagnosis, prophylaxis, and treatment of Lyme Disease, the inventors have identified and synthesized certain peptides corresponding to the epitopes of the antigenic proteins of *Borrelia*. These antigenic peptides are useful in diagnostics application to detect *Borrelia*-specific antibodies in Lyme disease patient biological samples. In another embodiment, these structure-based peptides induce a protective immune response (e.g., antibodies that are protective against *Borrelia* in animal models). These peptides thus are useful in Lyme disease vaccine compositions. Additionally, the inventors disclose a sonicated bacteria vaccine that does not induce antibody but demonstrates antibody-independent protection against Lyme disease.

In this specification, technical and scientific terms used herein have the same meaning as commonly understood by one of ordinary skill in the art to which this invention belongs and by reference to published texts, which provide one skilled in the art with a general guide to many of the terms used in the present application. The definitions contained in this specification are provided for clarity in describing the components and compositions herein and are not intended to limit the claimed invention.

As used herein, "subject" refers to any species that can be infected by *Borrelia burgdorferi*. In certain embodiments the subject is a human. In certain embodiments, the subject is a non-human animal. In certain embodiments the subject is bovine, equine, porcine, canine or a feline.

An "effective immunizing amount," as used herein, may vary depending upon the peptide(s), nucleic acid sequence(s), the *Borrelia* burgdorferi protein from which the peptide or nucleic acid sequence was derived, as well as depending upon the strain of *Borrelia burgdorferi* from which the peptides are derived, or which is used to generate the sonicate. In certain embodiment, the amount may be any amount sufficient to evoke a protective antibody-independent immune response. In another embodiments, the amount may be any amount sufficient to evoke an antibody response.

A "protective immune response" as used herein is an immune response in a subject that leads to protection against one or more indications of infection; and may span a range of effects from complete protection from any indication of *B. burgdorferi* infection to an immune response that permits reduction of symptoms of the underlying infection, after challenge. A protective immune response further includes elimination, reduction, or inhibition of one or more of the underlying cellular, physiological, or biochemical causes or mechanisms causing the symptoms. The pharmaceutical compositions described herein are intended to provide a protective immune response.

The term "percent identical" or "percent identity" refers to sequence identity between two amino acid sequences or two nucleic acid sequences. Identity can be determined by comparing a position in each sequence which may be aligned for purposes of comparison. When an equivalent position in the compared sequences is occupied by the same amino acid or nucleotide, then the amino acid or nucleic acid sequences are identical at that position. Expression as a percentage of identity refers to a function of the number of identical amino acids or nucleotides, or a derivative or variant thereof, at corresponding positions (e.g., as defined by an alignment) shared by the compared sequences. Various alignment algorithms and/or programs may be used to determine percent identity, non-limiting examples of which include FASTA, BLAST, or ENTREZ. FASTA and BLAST are available as a part of the GCG sequence analysis package (University of Wisconsin, Madison, WI), and can be used with, e.g., default settings. ENTREZ is available through the National Center for Biotechnology Information, National Library of Medicine, National Institutes of Health, Bethesda, MD.

As used herein, the term "biological sample" refers to, without limitation, material for testing obtain from a subject suspected of having Lyme Disease. These samples include blood, including serum, plasma, whole blood, and peripheral blood, saliva, urine, vaginal or cervical secretions, amniotic fluid, placental fluid, cerebrospinal fluid, or serous fluids, mucosal secretions (e.g., buccal, vaginal, or rectal). Still other samples include a blood-derived or biopsy-derived biological sample of tissue or a cell lysate (i.e., a mixture derived from tissue, e.g., heart and joints) and/or cells.

By the term "immobilization surface" is meant any surface on which the peptide or nucleic acid in question can be bound, as opposed to use in solution. A variety of immobilization surfaces are useful for diagnostic testing, such as glass, silicon, metal plastic, PDMS, nitrocellulose, or hydrogel. The surface, depending upon the reagent and number of reagents and assay can be a planar microchannel, a microfluidics card, a plate, a slide, a chip, a bead, a microarray, a strip, or a self-assembled monolayer. See, e.g., Kim D and Herr, A, 2013 July, Biomicrofluidics, 7(4):041501 for lists of other surfaces. Methods of immobilizing the peptides or nucleic acids, covalently or non-covalently to such immobilization surfaces are known in the art. For example, the peptide or nucleic acid sequence is attached to a selected surface resulting in reduction or loss of mobility via physical adsorption through charge-charge interaction or hydrophobic interaction, covalent bonding, Streptavidin-Biotin interaction, or affinity coupling, among other techniques.

As used herein, the term "detectable label" means a reagent, moiety, or compound capable of providing a detectable signal, depending upon the assay format employed. A label may be associated with one or more peptides or one or more nucleic acid sequences. Alternatively, different labels may be used for each peptide or nucleic acid in the reagent or kit. Such labels are capable, alone or in concert with other compositions or compounds, of providing a detectable signal. In one embodiment, the labels are desirably interactive to produce a detectable signal. Most desirably, the label is detectable visually, e.g. colorimetrically. A variety of enzyme systems operate to reveal a colorimetric signal in an assay, e.g., glucose oxidase (which uses glucose as a substrate) releases peroxide as a product that in the presence of peroxidase and a hydrogen donor such as tetramethyl benzidine (TMB) produces an oxidized TMB that is seen as a blue color. Other examples include horseradish peroxidase (HRP) or alkaline phosphatase (AP), and hexokinase in conjunction with glucose-6-phosphate dehydrogenase that reacts with ATP, glucose, and NAD+ to yield, among other products, NADH that is detected as increased absorbance at 340 nm wavelength. Still other label systems that may be utilized in the described methods and reagents are detectable by other means, e.g., colored latex microparticles (Bangs Laboratories, Indiana) in which a dye is embedded may be used in place of enzymes to provide a visual signal indicative of the presence of the labeled ligand or construct in applicable assays. Still other labels include fluorescent compounds, fluorophores, radioactive compounds, or elements. In one embodiment, a fluorescent detectable fluorochrome, e.g., fluorescein isothiocyanate (FITC), phycoerythrin (PE), allophycocyanin (APC), coriphosphine-O (CPO) or tandem dyes, PE-cyanin-5 or -7 (PC5 or PC7)), PE-Texas Red (ECD), PE-cyanin-5.5, rhodamine, PerCP, and Alexa dyes. Combinations of such labels, such as Texas Red and rhodamine, FITC+PE, FITC+PECyS and PE+PECy7, among others may be used depending upon assay method. The selection and/or generation of suitable labels for use in labeling the peptide or nucleic acid reagents and/or any component of diagnostic kit is within the skill of the art, provided with this specification.

The terms "a" or "an" refers to one or more. For example, "an expression cassette" is understood to represent one or more such cassettes. As such, the terms "a" (or "an"), "one or more," and "at least one" are used interchangeably herein.

As used herein, the term "about" means a variability of plus or minus 10% from the reference given, unless otherwise specified.

The words "comprise", "comprises", and "comprising" are to be interpreted inclusively rather than exclusively, i.e., to include other unspecified components or process steps. The words "consist", "consisting", and its variants, are to be interpreted exclusively, rather than inclusively, i.e., to exclude components or steps not specifically recited.

B. burgdorferi Structure

Borrelia burgdorferi is a Gram-negative spiral bacterium bound by an inner cytoplasmic membrane and an outer membrane. The outer membrane lacks lipopolysaccharide and consists of a lipid bilayer that is composed of phospholipids and glycolipids. Cholesterol glycolipids in the outer membrane form lipid-raft-like microdomains that change in order and size in response to temperature, which is an important environmental cue for B. burgdorferi during transmission between the tick vector and the mammalian host. The B. burgdorferi outer membrane also contains surface lipoproteins, which can change depending on the environment. The outer surface proteins of B. burgdorferi includes OspA, OspB, OspC, OspD, OspE, OspF, DbpA, DbpB, CspA, VlsE, BptA that are lipid-modified outer surface proteins anchored to the outer leaflet of the outer membrane through their lipid moieties. P13, P66, BesC, BamA, Lmp1 and BB0405 are outer surface proteins that have one or more transmembrane domains that anchor them into the outer membrane.

B. burgdorferi bacteria live in the midgut of ticks. In ticks, B. burgdorferi predominantly express the outer-surface protein A (OspA) before the blood meal, when the bacteria is in the midgut. OspA mediates the attachment of B. burgdorferi to the tick midgut by binding the midgut receptor TROSPA (Tick Receptor for OspA). When infected ticks feed blood meal, the spirochetes multiply within the gut, express high levels of OspC, migrate to the tick's salivary glands, and infect the vertebrate host. OspC has been shown to bind a tick salivary protein, Salp15, in vitro and in vivo, indicating a possible role for OspC in transmission and/or survival early during host colonization. Thus, OspA is required for colonizing the vector; whereas, OspC is required for infecting the host. OspF is identified as a potential adhesin and binds to organs of the human host. B. burgdorferi is able to persist in patients for extended periods and establish chronic infection in host tissues. VlsE as an important virulence determinant of B. burgdorferi.

The periplasmic flagella of B. burgdorferi is responsible for the flat-wave morphology of the bacteria. The flagella are attached to each cell pole and wind around the cell cylinder in the periplasmic space between the peptidoglycan layer and the outer membrane. Flagellar motors are located at the cell poles and are situated next to the methyl-accepting chemotaxis proteins that direct movement of the bacteria towards chemoattractants (including nutrients) and away from repellants including organic solvents.

The genome of the bacterium Borrelia burgdorferi, contains a linear chromosome of 910,725 base pairs and at least 17 linear and circular plasmids. The chromosome contains 853 genes encoding a basic set of proteins for DNA replication, transcription, translation, solute transport and energy metabolism.

B. burgdorferi has a very limited metabolic capacity and is highly dependent on its tick vector and vertebrate host for most essential factors. B. burgdorferi lacks genes encoding proteins that have a role in the tricarboxylic acid cycle and oxidative phosphorylation, and relies exclusively on glycolysis for energy production. For this purpose, B. burgdorferi uses several host or vector-derived carbohydrates, including glucose, glycerol, maltose, N-acetylglucosamine, trehalose and chitobiose. The B. burgdorferi genome also lacks genes that are required for the synthesis of amino acids, lipids, nucleotides and cofactors. To obtain these factors, the B. burgdorferi genome encodes 16 distinct membrane transporters, many of which have broad substrate specificity. Owing to the inability of B. burgdorferi to synthesize fatty acids, its lipid composition reflects that of the host tissues; B. burgdorferi exchanges lipids with the plasma membrane of eukaryotic cells, either through direct contact or via outer membrane vesicles.

Peptides and Nucleic Acid Sequences

Peptides useful in this invention were derived from *B. burgdorferi* outer surface proteins (Osp), i.e., specifically OspA, OspC, OspE, and OspF, VLSE, the neutrophil activating protein NapA, and proteins P41, P100 and the Laminin-binding *Borrelia* membrane protein A (BmpA) (see Example 1, Table 1 below). In one embodiment, the peptides are those identified as SEQ ID Nos: 10 to 18 (see Example 1, Table 2 below). In addition to the specified peptides

| | |
|---|---|
| KVTSKDKS STEEKFNEKG EVS | SEQ ID NO: 10 |
| NSGKDGNTSANSADESVKGP | SEQ ID NO: 11 |
| FILIGACKIHTSYDEQSSGESK | SEQ ID NO: 12 |
| VQDLESSEQNVKKTEQEIKK | SEQ ID NO: 13 |
| FFVFINCKSQVADKDDPTNKFY | SEQ ID NO: 14 |
| DKSFNESALNGVKKVKEEFK | SEQ ID NO: 15 |
| SYIKKDDLDAIQLKLQELLASL | SEQ ID NO: 16 |
| LSKTQEKLSSGYRINRASDDA | SEQ ID NO: 17 |
| YKGPYDSTNTYEQIVGIGEFLAR, | SEQ ID NO: 18 | other related peptides that may be useful in the reagents and compositions described herein.

One related peptide is a peptide having at least 90% identity to a specifically identified peptide. The phrase "at least 90% identity" is intended to include peptides having percent identities of 91, 92, 93, 94, 95, 96, 97, 99 and 99% as well as complete 100% identify with the specified peptide. In one embodiment, a peptide having at least 90% identity to a peptide of SEQ ID NO: 10 may be a usual peptide for diagnostic or therapeutic use. In another embodiment, a peptide having at least 90% identity to a peptide of SEQ ID NO: 11 may be a usual peptide for diagnostic or therapeutic use. In another embodiment, a peptide having at least 90% identity to a peptide of SEQ ID NO: 12 may be a usual peptide for diagnostic or therapeutic use. In another embodiment, a peptide having at least 90% identity to a peptide of SEQ ID NO: 13 may be a usual peptide for diagnostic or therapeutic use. In another embodiment, a peptide having at least 90% identity to a peptide of SEQ ID NO: 14 may be a usual peptide for diagnostic or therapeutic use. In another embodiment, a peptide having at least 90% identity to a peptide of SEQ ID NO: 15 may be a usual peptide for diagnostic or therapeutic use. In another embodiment, a peptide having at least 90% identity to a peptide of SEQ ID NO: 16 may be a usual peptide for diagnostic or therapeutic use. In another embodiment, a peptide having at least 90% identity to a peptide of SEQ ID NO: 17 may be a usual peptide for diagnostic or therapeutic use. In another embodiment, a peptide having at least 90% identity to a peptide of SEQ ID NO: 18 may be a usual peptide for diagnostic or therapeutic use.

Another related peptide is a peptide variant that differs from a specific peptide of SEQ ID NO: 10-18 by one or more conservative substitutions or replacements. For example, a conservative substitute is an amino acid replacement that changes a given amino acid to a different amino acid having similar biochemical properties, e.g., charge, hydrophobicity, and size). Such conservative amino acids include Met, Ile, Leu, and Val; or Phe with Trp; or Asp with Glu; or Lys with Arg; of His, Asp, Gln, Ser, Thr and Tyr. See, e.g., Betts M R and Russell R B, Amino Acid Properties and Consequences of Substitutions" in Bioinformatics for Geneticists, Eds. Barnes M R and Gray I C, 2003 John Wiley & Sons, Ltd.

Another related peptide is a peptide variant differing in one or more naturally occurring amino acids from a peptide of SEQ ID NO: 10-18, based upon the strain of *B. burgdorferi* from which the peptide sequence is derived.

Any nucleic acid sequence that encodes one or more of peptides SEQ ID NO: 10-18 or their related peptides as defined above is included in the compositions described herein. Because the genetic code is degenerate, one of skill in the art can construct a variety of differing nucleic acid sequences that can encode the same peptide. Thus, in embodiments of the compositions and methods described herein, it is understood that all nucleic acid sequences encoding the same peptides can be employed. Similarly, the encoding nucleic acid sequences can encode multiples of the same or multiple different peptides in a single sequence, if desired.

Diagnostic Reagents and Methods

Thus, diagnostic reagents as disclosed herein can include an individual peptide or multiple peptides as defined herein. The multiple peptides can be present in a simple mixture or prepared as fusion proteins; or fused to carriers or immobilization surfaces or linked to detectable labels. The diagnostic compositions may contain multiple copies of at least 2, 3, 4, 5, 6, 7, 8, 9 or at least 10 different peptides from SEQ ID Nos 10-18 or related peptides. In other embodiments, optional amino acids (e.g., -Gly-Ser-, or Pro-Ala or other equivalents) or chemical compound spacers may be included at the termini of the peptides for linking the peptides together or to a carrier or to an immobilization surface. The reagents may contain mixtures or individual peptides. Still other reagents can include peptides that contain fusions of two or more of SEQ ID Nos: 10-18. Still other suitable related peptides can be SEQ ID NO: 10-18 to which modifications are made on the N or C terminus. These peptides described herein may be produced synthetically or recombinantly. The reagent composition may take the form of one or more of the above-described peptides expressed as a synthetic peptide coupled to a carrier protein. Alternatively, a composition may contain multiple peptides, each expressed as a multiple antigenic peptide, optionally coupled to carrier protein. Alternatively, the selected peptides may be linked sequentially and expressed within a recombinantly produced protein.

By "mixture" is meant any combination of two or more different peptides (including, e.g., any of the variants or sequences that share at least 90% identity with the reference sequence or are natural variants or contain conservative replacements). In one embodiment, the reagent contains SEQ ID Nos.: 10 and 11, or 10 and 12, or 10 and 13, or 10 and 14, or 10 and 15, or 10 and 16, or 10 and 17, or 10 and 18, or 11 and 12, 11 and 13, or 11 and 14, or 11 and 15, or 11 and 16, or 11 and 17, or 11 and 18, or 12 and 13, or 12 and 14, or 12 and 15, or 12 and 16, or 12 and 17, or 12 and 18, or 13 and 14, or 13 and 15, or 13 and 16, or 13 and 17, or 13 and 18, or 14 and 15, or 14 and 16, or 14 and 17, or 14 and 18, or 15 and 16, or 15 and 17, or 15 and 18, or 16 and 17, or 16 and 18, or 17 and 18 (including, e.g., any of the variants or sequences that share at least 90% identity with the reference sequence, or are natural variants or contain conservative replacements). In another embodiment, the reagent contains SEQ ID Nos: 10, 11 and 12, or 10, 11 and 13, or 10, 11 and 14, or 10, 11 and 15, or 10, 11 and 16; or 10, 11 and 17, or 10, 11 and 18, or 10, 12, and 13, or 10, 12 and 14, or 10, 12 and 15, or 10, 12 and 16; or 10, 12 and 17, or 10, 12 and 18, or 10, 13, and 14, or 10, 13 and 15, or 10, 13 and 16; or 10, 13 and 17, or 10, 13 and 18, or 10, 14 and 15, or 10, 14 and 16; or 10, 14 and 17, or 10, 14 and 18 or 10, 15 and 16; or 10, 15 and 17, or 10, 15 and 18; or 10, 16 and 17, or 10, 16 and 18; or 10, 17 and 18; or 11, 12 and 13, or 11, 12 and 14, or 11, 12 and 15, or 11, 12 and 16; or 11, 12 and 17, or 11, 12 and 18, or 11, 13 and 14, or 11, 13 and 15, or 11, 13 and 16; or 11, 13 and 17, or 11, 13 and 18, or 11, 14 and 15, or 11, 14 and 16; or 11, 14 and 17, or 11, 14 and 18, or 11, 15 and 16; or 11, 15 and 17, or 11, 15 and 18, or 11, 16 and 17, or 11, 16, and 18; or 11, 17 and 18; or 12, 13 and 14, or 12, 13 and 15, or 12, 13 and 16; or 12, 13 and 17, or 12, 13 and 18, or 12, 14 and 15, or 12, 14 and 16; or 12, 14 and 17, or 12, 14 and 18, or 12, 15 and 16; or 12, 15 and 17, or 12, 15 and 18, or 12, 16 and 17, or 12, 16 and 18 or 12, 17 and 18; 13, 14 and 15, or 13, 14 and 16; or 13, 14 and 17, or 13, 14 and 18, or 14, 15, and 16, or 14, 15 and 17, or 14, 15 and 18; or 15, 16 and 17; or 15, 16 and 18; or 16, 17 and 18 (including, e.g., any of the variants or sequences that share at least 90% identity with the reference sequence, or are natural variants or contain conservative replacements).

In another mixture, the reagents include 4 peptides, including any combination of 4 peptides from SEQ ID No. 10-18 and any of the variants or sequences that share at least 90% identity with the reference sequence, or are natural variants or contain conservative replacements. In another mixture, the reagents include 5 peptides, including any combination of 5 peptides from SEQ ID No. 10-18 and any of the variants or sequences that share at least 90% identity with the reference sequence, or are natural variants or contain conservative replacements. In another mixture, the reagents include 6 peptides, including any combination of 6 peptides from SEQ ID No. 10-18 and any of the variants or sequences that share at least 90% identity with the reference sequence, or are natural variants or contain conservative replacements. In another mixture, the reagents include 7 peptides, including any combination of 7 peptides from SEQ ID No. 10-18 and any of the variants or sequences that share at least 90% identity with the reference sequence, or are natural variants or contain conservative replacements. In another mixture, the reagents include 8 peptides, including any combination of 8 peptides from SEQ ID No. 10-18 and any of the variants or sequences that share at least 90% identity with the reference sequence, or are natural variants or contain conservative replacements. In another mixture, the reagents include 9 peptides, including any combination of 9 peptides from SEQ ID No. 10-18 and any of the variants or sequences that share at least 90% identity with the reference sequence, or are natural variants or contain conservative replacements. In another mixture, the reagents include greater than 9 peptides, including any combination of >9 peptides from SEQ ID No. 10-18 and any of the variants or sequences that share at least 90% identity with the reference sequence, or are natural variants or contain conservative replacements.

Another form of diagnostic reagent depending upon the assay technique being used is a nucleic acid sequence that encodes one or more of peptides SEQ ID NO: 10-18 or their related peptides as defined above is included in the reagent compositions described herein. Such reagents can include nucleic acid sequences encoding multiple repetitions of a single peptide or multiple of the peptides in a fusion and may be produced by conventional synthetic or recombinant techniques. The multiple peptides may be selected from those mixtures described above.

In other embodiments of the reagents, one or more of the peptides or nucleic acid molecules is covalently or noncovalently joined to an immobilization surface, as defined above. Still other reagents include one or more of said peptides or nucleic acid molecules covalently or noncovalently joined to a labeling moiety capable alone or in combination with one or more additional molecules of generating a detectable signal. Examples of such labels and immobilization surfaces are described above.

Where the reagent is a nucleic acid sequence, such sequence can be labeled by suitable techniques or bound to immobilization surfaces by conventional binding techniques. Such nucleic acid sequences can be incorporated into plasmid or viral vectors, for recombinant expression by now common techniques known to one of skill in the art. See, textbooks such as Maniatis, T., et al (1982). Molecular cloning: a laboratory manual. Cold Spring Harbor, N.Y., Cold Spring Harbor Laboratory and others. In one embodiment, the DNA sequences can be employed as hybridization probes in hybridization assays. In other embodiment, the sequences can be employed as primers.

Diagnostic kits can include any of the above recited peptides or nucleic acid sequences, as wells immobilization surfaces, reagents for accomplishing the immobilization and other physical and chemical apparatus for performing the diagnostic assay of choice. In addition to the reagents above, alternatively, a diagnostic kit thus also contains miscellaneous reagents and apparatus for reading labels, e.g., certain substrates that interact with an enzymatic label to produce a color signal, etc., apparatus for taking blood samples, as well as appropriate vials and other diagnostic assay components.

The particular assay format used to measure the infection of a subject by *B. burgdorferi* may be selected from among a wide range of immunoassays to identify anti-*B. burgdorferi* antibodies, such as enzyme-linked immunoassays, sandwich immunoassays, homogeneous assays, immunohistochemistry formats, or other conventional assay formats. One of skill in the art may readily select from any number of conventional immunoassay formats. Other assays include high pressure liquid chromatography (HPLC), immunohistochemistry, etc. In one embodiment, the diagnostic method is an Enzyme-Linked Immunosorbent Assay. Other suitable assay formats include detection protocols, including without limitation, PCR, Immuno-PCR and proximity ligation or proximity extension assay protocols, PEA, RCA, sequencing, and fluorescence hybridization protocols. There are a variety of assay formats known to the skilled artisan for using a ligand to detect a target molecule in a sample. (For example, see Harlow and Lane, Antibodies: A Laboratory Manual, Cold Spring Harbor Laboratory, 1988).

Thus, a method of diagnosing Lyme borreliosis in a subject, comprises contacting in vitro a biological sample from the subject with a peptide reagent or nucleic reagent such as described herein. The presence of an antibody that binds *Borrelia* is detected by the complex formed between the reagent and the antibody in the sample. Detection or measurement of the sample antibody to *Borrelia* may be obtained by use of a variety of apparatus or machines, such as computer-programmed instruments that can transform the detectable signals generated from the diagnostic reagents complexed with the antibody in the biological sample into numerical or graphical data useful in performing the diagnosis. Such instruments may be suitably programmed to permit the comparison of the measured antibody in the sample with the appropriate reference standard and generate a diagnostic report or graph that can indicate a diagnosis of infection, i.e., Lyme Disease.

In fact, as described in the examples, one assay format/method of diagnosis involved coating multiple of the peptides of SEQ ID NO: 10-18 on an ELISA plate; and incubating same with the blood samples of patients and controls. They were then probed with the secondary antibodies conjugated to horseradish peroxidase, for use in generating a detectable signal if antibodies in the sample bound to the peptides on the plate, indicating the presence of antibodies to *B. burgdorferi*. The data in the examples demonstrated that the tested peptides are useful in the diagnosis of *Borrelia* in patients. The peptides are also potential vaccine candidates and could be used to protect against *Borrelia*.

Other assay formats may be employed using the reagents described herein to detect Lyme Disease in biological samples.

Pharmaceutical Compositions and Methods

The peptides described above and nucleic acid sequences encoding them are also useful in pharmaceutical composition and methods for treating, retarding or prevention Lyme Disease in subjects. In one embodiment a pharmaceutical composition includes the selected peptide(s) of SEQ ID NO: 10-18 or a related peptide as described herein. In another embodiment, the pharmaceutical composition employs mixtures of different peptides (e.g., mixtures of 2 through greater than 9, as described above for the diagnostic reagents). In another embodiment a pharmaceutical composition includes one or more nucleic acid sequences encoding one or more selected peptide(s) of SEQ ID NO: 10-18 or a related peptide as described herein. In another embodiment, the pharmaceutical composition employs mixtures of nucleic acid sequences encoding different peptides. Each pharmaceutical composition comprises the active component (peptide and/or nucleic acid) in an effective amount to induce an immune response and/or reduce the spread of infection and/or prevent an initial or repeated infection. In other embodiments, each composition includes a pharmaceutically acceptable carrier, excipient, or adjuvant.

By "pharmaceutically acceptable carrier or excipient" is meant a solid and/or liquid carrier, in in dry or liquid form and pharmaceutically acceptable. The compositions are typically sterile solutions or suspensions. Examples of excipients which may be combined with the antagonist or inhibitor include, without limitation, solid carriers, liquid carriers, adjuvants, amino acids (glycine, glutamine, asparagine, arginine, lysine), antioxidants (ascorbic acid, sodium sulfite or sodium hydrogen-sulfite), binders (gum tragacanth, acacia, starch, gelatin, polyglycolic acid, polylactic acid, poly-d,l-lactide/glycolide, polyoxaethylene, polyoxapropylene, polyacrylamides, polymaleic acid, polymaleic esters, polymaleic amides, polyacrylic acid, polyacrylic esters, polyvinylalcohols, polyvinylesters, polyvinylethers, polyvinylimidazole, polyvinylpyrrolidon, or chitosan), buffers (borate, bicarbonate, Tris-HCl, citrates, phosphates or other organic acids), bulking agents (mannitol or glycine), carbohydrates (such as glucose, mannose, or dextrins), clarifiers, coatings (gelatin, wax, shellac, sugar or other biological degradable polymers), coloring agents, complexing agents (caffeine, polyvinylpyrrolidone, β-cyclodextrin or hydroxypropyl-β-cyclodextrin), compression aids, diluents, disintegrants, dyes, emulsifiers, emollients, encapsulating materials, fillers, flavoring agents (peppermint or oil of wintergreen or fruit flavor), glidants, granulating agents, lubricants, metal chelators (ethylenediamine tetraacetic acid (EDTA)), osmo-regulators, pH adjustors, preservatives (benzalkonium chloride, benzoic acid, salicylic acid, thimerosal, phenethyl alcohol, methylparaben, propylparaben, chlorhexidine, sorbic acid, hydrogen peroxide, chlorobutanol, phenol or thimerosal), solubilizers, sorbents, stabilizers, sterilizer, suspending agent, sweeteners (mannitol, sorbitol, sucrose, glucose, mannose, dextrins, lactose or aspartame), surfactants, syrup, thickening agents, tonicity enhancing agents (sodium or potassium chloride) or viscosity regulators. See, the excipients in "Handbook of Pharmaceutical Excipients", 5$^{th}$ Edition, Eds.: Rowe, Sheskey, and Owen, APhA Publications (Washington, DC), 2005 and U.S. Pat. No. 7,078,053, which are incorporated herein by reference. The selection of the excipient is dependent on the nature of the compound selected and the form of administration desired.

Solid carriers include, without limitation, starch, lactose, dicalcium phosphate, microcrystalline cellulose, sucrose and kaolin, calcium carbonate, sodium carbonate, bicarbonate, lactose, calcium phosphate, gelatin, magnesium stearate, stearic acid, or talc. Fluid carriers without limitation, water, e.g., sterile water, Ringer's solution, isotonic sodium chloride solution, neutral buffered saline, saline mixed with serum albumin, organic solvents (such as ethanol, glycerol, propylene glycol, liquid polyethylene glycol, dimethylsulfoxide (DMSO)), oils (vegetable oils such as fractionated coconut oil, arachis oil, corn oil, peanut oil, and sesame oil; oily esters such as ethyl oleate and isopropyl myristate; and any bland fixed oil including synthetic mono- or diglycerides), fats, fatty acids (include, without limitation, oleic acid find use in the preparation of injectables), cellulose derivatives such as sodium carboxymethyl cellulose, and/or surfactants.

Examples of pharmaceutically acceptable adjuvants are well known in the art, see, e.g. REMINGTON'S PHARMACEUTICAL SCIENCES, 18th Ed. (1990, Mack Publishing Co., Easton, Pa.) and GOODMAN AND GILMAN'S, THE PHARMACOLOGICAL BASIS OF THERAPEUTICS (10th ed. 2001). In certain embodiments, suitable adjuvants include the AddaVax™ adjuvant used in the examples or Aluminum salts, such as aluminum hydroxide, aluminum phosphate, and aluminum potassium sulfate, Monophosphoryl lipid A, tetanus toxoid, cholera toxin B subunit, adenylate cyclase mutant, pertussis toxin mutant, and lipopolysaccharide, among other known adjuvants.

Thus, the pharmaceutical compositions may be in any form, i.e., a liquid, emulsion, dried powder, including as a lyophilized powder, and/or in a mist. In certain embodiments, the composition vaccine is lyophilize.

By "effective amount" is meant the amount or concentration (by single dose or in a dosage regimen delivered per day) of the peptide or nucleic acid composition sufficient to retard, suppress or inhibit *B. burgdorferi* infection, while providing the least negative side effects to the treated subject. In one embodiment, the effective amount of the peptide composition is within the range of 1 mg/kg body weight to 100 mg/kg body weight in humans including all integers or fractional amounts within the range. In certain embodiments, the effective amount is at least 2, 5, 10, 15, 20, 25, 30, 35, 40, 45, 50, 55, 60, 65, 70, 75, 80, 85, 90, 95 or 100 mg/kg body weight, including all integers or fractional amounts within the range. In one embodiment, the above amounts represent a single dose. In another embodiment, the above amounts define an amount delivered to the subject per day. In another embodiment, the above amounts define an amount delivered to the subject per day in multiple doses. In still other embodiments, these amounts represent the amount delivered to the subject over more than a single day. The nucleic acid compositions can be delivered in appropriate doses depending upon whether they are present as viral vectors, plasmid vectors and/or "naked DNA". Selection of such dosages is within the skill of the art.

Therefore, in another aspect, a method for treating, inhibiting, or preventing Lyme Disease involves administering an effective amount of one of pharmaceutical compositions described herein to a subject. The administration is at a dosage or combination of dosages forming an amount effective to prevent or treat Lyme Disease. In another embodiment, the peptide(s) pharmaceutical composition or nucleic acid sequence(s) pharmaceutical composition described herein can also administered in combination with another an antibiotic or other pharmaceutical component designed to treat other aspects of the Lyme Disease infection.

Conventional and pharmaceutically acceptable routes of administration include, but are not limited to, systemic routes, such as intraperitoneal, intravenous, intranasal, intravenous, intramuscular, intratracheal, subcutaneous, and other parenteral routes of administration. In one embodiment, the route of administration is oral. In another embodiment, the route of administration is intraperitoneal. In another embodiment, the route of administration is intravascular. Routes of administration may be combined, if desired. In some embodiments, the administration is repeated periodically.

Vaccine Sonicate and Methods of Use

In addition to the peptide/nucleic acid compositions described above, another a pharmaceutical composition for the treatment, inhibition, or prophylaxis of Lyme borreliosis comprises a sonicate of a *Borrelia* strain. In one embodiment, the sonicate is present in an amount sufficient to elicit an antibody independent protective immune response.

In one embodiment, a *Borrelia* sonicate is obtained by growing *Borrelia. burgdorferi*, a selected strain or another Lyme Disease causing *Borrelia* species in a cell or cell line to produce the source *B. burgdorferi* for sonication, isolating the bacteria, and subjecting the isolated *Borrelia* to sonication. In certain aspects the present invention includes a composition that comprises an inactive *Borrelia* sonicate. The immunogenic compositions and/or vaccines of the present invention can further include an adjuvant or other excipient, as above described. See, e.g., similar methods disclosed in US Published Patent Application No. 2016/010625, incorporated by reference herein.

In general, after isolation bacteria are subjected to ultrasound treatment in liquid medium, at a frequency and intensity and for such duration as to rupture essentially all the bacteria, without at the same time raising the temperature of the bacterial solution sufficiently to significantly denature components of the sonicated lysate. In certain aspects treatment in the liquid medium with sound waves at an appropriate frequency and of sufficiently high-power level produces cavitation, whereby the structure of the bacteria in the liquid is disrupted and dispersed. Cavitation produces violent pressure changes in the sonicated liquid at multiple microscopically spaced volume elements within the liquid. These pressure changes, which may be thousands of atmospheres in magnitude, break up any clusters of cells as well as disintegrate the cells themselves, if the cavitation is sufficiently intense, and shear their genetic material, deoxyribonucleic acid (DNA), or ribonucleic acid (RNA). The destructive force of the cavitation depends upon the surface tension of the sonicated liquid and the vapor pressure as well as the magnitude of the change in bubble size, which in turn depends upon the sound intensity and wave length. Other considerations include the effect of dissolved gases in the liquid and the control of temperature during the procedure.

In one embodiment, the frequency, intensity, and duration of the sonication is to disintegrate the bacteria cells without raising the temperature of the liquid. In addition, the DNA or RNA of the bacteria which encodes their genetic information is sheared and is no longer capable of directing cellular replication. The completeness of the disruption of the cells can be determined by known methods including the use of microscopic examination and attempted growth of bacteria from the sonicated preparation.

In one embodiment, the sonic waves are introduced into the liquid medium at a frequency of about 20 to about 40 kHz. The minimum intensity (power) of the sonic waves should be about 1 watt/cm$^2$ when utilizing a 20 kHz frequency. At this minimum level of power, cavitation is initiated. In one embodiment, the intensity level at about 20 kHz is 50 to 175 watts/cm$^2$. The destructive power of the sonic waves varies as a function of the frequency of the sonic waves used, with a lower effect being produced at higher frequencies.

In certain embodiments, the bacteria samples can be pulsed for about 15 seconds at about setting 4-5 (about 25% of output of sonicator, available from Rx Technologies, Inc., Garden City, N.Y., U.S.A.) and then rested for about 60 seconds in an ice bath. The sample is further sonicated for an additional 3 pulses (about 15 seconds). In general, the duration of sonication may range from about 10 seconds to several minutes or longer and most preferably is performed in at least two installments for about 15 seconds or longer. The sonication duration and intensity schedule are provided which results in maximum lysis and removes any viable bacteria from the sonicate.

After sonication of the bacteria the resulting product (a sonicate) is directly available for use as a pharmaceutical composition or vaccine. No further additions or purification of the resulting material is necessary. Alternatively, the sonicated material can be added to a pharmaceutically acceptable carrier or adjuvant. Suitable pharmaceutically acceptable carriers will be apparent to those skilled in the art, as described.

Thus, in one aspect a method of treating, preventing, or retarding infection by *B. burgdorferi* comprises administering an effective amount of the *B. burgdorferi* sonicate to a subject in need thereof, wherein said sonicate elicits an antibody-independent protective immune response. The sonicate vaccines may be administered as a liquid, emulsion, dried powder, including as a lyophilized powder, and/or in a mist through any suitable parenteral route, intravenously, intraperitoneally, intradermally, by scarification, subcutaneously, intramuscularly, or inoculated by a mucosal route, e.g., orally, intranasally, as an aerosol, by eye drop, or implanted as a freeze-dried powder.

Dosages of the *Borrelia* (e.g., *B. burgdorferi*) associated with adjuvants and/or carriers will often be about that of the immunogenic material (disrupted bacteria) alone. For use as human vaccines, dosages will be set by the prescribing physician considering relevant factors including the age, weight and condition of the patient and the pharmacokinetics of the agent and release characteristics of the agent from pharmaceutical dosage forms. In one embodiment the vaccine will generally contain an amount of protein ranging from about 25 micrograms to about 5 milligrams. Thus, the amount of protein used will fall within this range. The amount of protein contained in any sonicate can be generally assayed by the methods of Bradford, Anal. Biochem., 72,248 (1976) or Lowry, J. Biol. Chem., 193, 265 (1951).

Lyme Disease

Lyme Disease is caused by *Borrelia burgdorferi* (or other *Borrelia* species) transmitted by ticks. Human infection can result in musculoskeletal, neurologic or cardiovascular disorders, which are normally present in three phases: (1) early localized disease; (2) early disseminated disease; and (3) late Lyme disease. The clinical features of each phase can overlap, and some patients present in later phases of the disease without previously having symptoms of earlier phases of the disease. Early localized disease generally states within two weeks of the tick bite and often starts with a characteristic skin rash called erythema migrans (EM). The disease progresses to the second early disseminated state where the EM rash is followed by Spirochetemia caused by early wide-spread dissemination of the bacteria through tissue and body fluids. This second stage may be accompanied by one or more additional skin lesions, fatigue, myalgia, arthralgia, neurologic and cardiac symptoms. Left untreated, the disease progresses to late Lyme disease where chronic major manifestations occur. Late stage Lyme disease is characterized by arthritis, encephalomyelitis and/or peripheral neuropathy, and potentially other symptoms. Approximately 25,000 to 30,000 cases of Lyme disease are reported in the United States annually, with CDC estimates of actual incidence reaching ten times that amount in view of underreporting; additional cases have also been reported in Europe and Asia.

In certain embodiments, the compositions and methods described herein are capable of detecting and/or treating Lyme disease in the early localized disease phase, the early disseminated disease phase, or the late Lyme disease phase. In certain embodiments, the patient is symptomatic. In certain embodiments, the patient is asymptomatic. In certain embodiments the patient does not have erythema migrans before or after being diagnosed.

Clinical diagnosis of Lyme disease is usually based on a typical EM rash in the early stage of the disease, and treatment of the disease with oral antibiotics: is generally effective at the early stage. However, the EM rash can be either missed (e.g., it usually disappears in a few days) or not present in an infected person (e.g., occurs in 70-80% of infected people). Without a confirmed EM rash, a clear diagnosis of Lyme disease can be difficult for a number of reasons, one of which is lack of specific signs and symptoms. For example, Lyme disease may mimic other conditions, such as chronic fatigue, multiple sclerosis, rheumatoid arthritis, and other diseases with multiple symptoms involving different body systems. In certain embodiments, the compositions and methods described herein are capable of treating complications and symptoms caused by Lyme disease. In certain embodiments, the compositions and methods described herein are capable of halting the progression of Lyme disease prior to the patient developing serious complications or chronic symptoms.

Arthritis is a prominent manifestation in patients with Lyme disease. The majority of individuals with Lyme disease have the HLA-DRB1*0401 or HLA-DRB1*0101 allele; these alleles also occur more frequently in patients with rheumatoid arthritis. HLA-DRB1 belongs to MHC II and is recognized by T cell, We have selected the epitope regions of the antigenic proteins that bind to HLA-DRB1.

EXAMPLES

The following examples disclose specific embodiments of diagnostic and prophylactic reagents for the diagnosis of and prevention or treatment of *Borrelia* infection.

Example 1: Identification of B Cell Epitope Peptides of *Borrelia*

We determined the epitopes of the antigenic proteins of *Borrelia* OspA, OspC, OspE, OspF, VlsE, BmpA, napA, p41, and p100 using a bioinformatice approach (FIGS. 1A-1D and Table 1). To determine a protein sequence for potential antigenic epitopes, sequences that are hydrophilic, surface-oriented, and flexible are selected. Most naturally occurring proteins in aqueous solutions have their hydrophilic residues on the protein surface and hydrophobic residues buried in the interior. We selected protein sequences that had good hydrophilicity as predicted by the Lasergene software (DNAStar, WI, USA). Highlighted sequences demonstrate peptides for use as diagnostic, treatment or vaccine compositions.

TABLE 1

Outer Surface Protein Sequences of *B. burgdorf* antigenic proteins

| Protein | Amino Acid Sequence | | | | SEQ ID NO |
|---|---|---|---|---|---|
| OspA | MKKYLLGIGL | ILALIACKQN | VSSLDEKNSV | SVDLPGEMKV | 1 |
|  | LVSKEKNKDG | KYDLIATVDK | LELKGTSDKN | NGSGVLEGVK |  |
|  | ADKSKVKLTI | SDDLGQTTLE | VFKEDGKTLV | SKKVTSKDKS |  |
|  | STEEKFNEKG | EVSEKIITRA | DGTRLEYTGI | KSDGSGKAKE |  |
|  | VLKGYVLEGT | LTAEKTTLVV | KEGTVTLSKN | ISKSGEVSVE |  |
|  | LNDTDSSAAT | KKTAAWNSGT | STLTITVNSK | KTKDLVFTKE |  |
|  | NTITVQQYDS | NGTKLEGSAV | EITKLDEIKN | ALK |  |
| OspC | MKKNTLSAIL | MTLFLFISCN | NSGKDGNTSA | NSADESVKGP | 2 |
|  | NLTEISKKIT | ESNAVVLAVK | EVETLLASID | EVAKKAIGNL |  |
|  | IAQNGLNAGA | NQNGSLLAGA | YVISTLIAEK | LDGLKNSEEL |  |
|  | KEKIEDAKKC | NKAFTDKLKS | SHAELGIANG | AATDANAKAA |  |
|  | ILKTNGTKDK | GAQELEKLFE | SVKNLSKAAQ | ETLNNSVKEL |  |
|  | TSPVVAESPK | KP |  |  |  |
| OspE | MNKKMKMFIV | YAVFILIGAC | KIHTSYDEQS | SGESKVKKIE | 3 |
|  | FSKFTVKIKN | KDKSGNWTDL | GDLVVRKEEN | GIDTGLNAGG |  |
|  | HSATFFSLEE | EVVNNFVKVM | TEGGSFKTSL | YYGYKEEQSV |  |
|  | INGIQNKEII | TKIEKIDGTE | YITFSGDKIK | NSGDKVAEYA |  |
|  | ISLEELKKNL | K (171) |  |  |  |

TABLE 1-continued

Outer Surface Protein Sequences of *B. burgdorf* antigenic proteins

| Protein | Amino Acid Sequence | SEQ ID NO |
|---|---|---|
| OspF | MNKKMFIICA VFALIISCKN YATSKDLEGA VQDLESSEQN VKKTEQEIKK QVEGFLEILE TKDLNKLDTK EIEKRIQELK EKIEKLDSKK TSIETYSEYE EKLKQIKEKL KGKADLEDKL KGLEDSLKKK KEERKKALED AKKKFEEFKG QVGSATGVTT GHRAGNQGSI GAQAWQCANS LGLGVSYSSS TGTDSNELAN KVIDDSIKKI DEELKNTIEN NGEVKKE | 4 |
| OSP VlsE | MNTKKISSAI LLTTFFVFIN CKSQVADKDD PTNKFYQSVI QLGNGFLDVF TSFGGLVAEA FGFKSDPKKS DVKTYFTTVA AKLEKTKTDL NSLPKEKSDI SSTTGKPDST GSVGTAVEGA IKEVSELLDK LVKAVKTAEG ASSGTAAIGE VVDNAAAAKA ADKDSVTGIA KGIKEIVEAA GGSKKLKAAA AKGENNKGAG KLFGKAGDAA HGDSEAASKA AGAVSAVSGE QILSAIVKAA AAGDQEGKKP GEAKNPIAAA IGEGDGDAEF NQDGMKKDDQ IAAAIALRGM AKDGKFAVKN DEKGKAEGAI KGAAESAVRK VLGAITGLIG DAVSSGLRKV GDSVKAASKE TPPALNK | 5 |
| NapA | MEKYLSYIKK DDLDAIQLKL QELLASLHIF YSNLRGIHWN IKDTNFFVIH KKTQKLYEYI EKIIDIVAER SRMLGYDSEF RYSEFMKKSF IKELDIESTS NFLPSMESIV CSLTEILKNI FGMRKLIDTA GDYGTANIMD DIMSDLEKHL WMHKALLENC DCFCHDENES KCCECDAK | 6 |
| P41 | MIINHNTSAI NASRNNAINA ANLSKTQEKP SSGYRINRAS DDAAGMGVSG KINAQIRGLS QASRNTSKAI NFIQTTEGNL NEVEKVLVRM KELAVQSGNG TYSDSDRGSI QIEIEQLTDE INRIADQAQY NQMHMLSNKS ASQNVKTAEE LGMQPAKINT PASLSGSQAS WTLRVHVGAN QDEAIAVNIY SANVANLFAG EGAQAAQAAP VQEGAQEEGA QQPTPATAPS QGGVNSPVNV TTTVDANTSL AKIENAIRMI SDQRANLGAF QNRLESIKNS TEYAIENLKA SYAQIKDATM TDEVVAATTK SILTQSAMAM IAQANQVPQY VLSLLR | 7 |
| P100 | MKELDKEKLR DFVNMDLEFV NYKGPYDSTN TYEQIVGIGE FLARPLINSN SNSIYYGKYF INRFIDDQDK KASVDVFSIG SRSQLDSILN LRRILTGYLI KSFDYERSSA ELIAKVITIH NAVYRGDLNY YKEVYIEAAL KSLTKENAGL SRVYSQWAGK TQIFIPLKKN ILSGKVESDI DIDSLVTDKV VAALLSENEA GVNFARDITD IQGETHKADQ DKIDIELDNV HKSDSNITET IENLRDQLEK ATDEEHRKEI ESQVDAKKKQ KEELDKKAID LDKAQQKLDS SEDNLDIQRD TVREKIQEDI DEINKEKNLP KPGDVSSPKV DKQLQIKESL EDLQEQLKET SDENQKREIE KQIEIKKSDE ELLKSKDPKA LDLNGDLNSK VSSKEKIKGK EGEIVKEESK ASLADLNNDE NLMRPEDQKL SEDKKLDSKK NLKPVSEIER VNEISKSNNN EISESSPLYK PSYSDMDSKE GIDNKDVNLQ ETKSQTKSQP TSLNQDLTTM SIDSSNPVFL EVIDPITNLG TLQLIDLNTG VRLKESTQQG IQRYGIYERE KDLVVIKMDS GKAKLQILNK LENLKVISES NFEINKNSSL YVDSKMILVV VKDSGNVWRL AKFSPKNLNE FILSENKILP FTSFSVRKNF IYLQDEFKSL ITLDLNTLKK VK | 8 |
| BmpA | MNKILLLILL ESIVFLSCSG KGSLGSEIPK VSLIIDGTFD DKSFNESALN GVKKVKEEFK IELVLKESSS NSYLSDLEGL KDAGSDLIWL IGYRFSDVAK VAALQNPDMK YAIIDPIYSN DPIPANLVGM TFRAQEGAFL TGYIAARLSK TGKIGFLGGI EGEIVDAFRY GYEAGAKYAN KDIKIFTQYI GSFADLEAGR SVATRMYSDE IDIIHHAAGL GGIGAIEVAK ELGSGHYIIG VDEDQAYLAP DNVITSTTKD VGRALNIFTS NHLKTNTFEG GKLINYGLKE GVVGFVRNPK MISFELEKEI DNLSSKIINK EIIVPSNKES YEKFLKEFI | 9 |

Example 2: Lyme Disease Detection—ELISA Assay

The following peptides identified in Table 2 were selected as epitopes of the N-terminal *B. burgdorferi* proteins of Table 1 for peptide synthesis. We synthesized the following peptides (GenScript) reported in Table 2:

TABLE 2

Peptides from *Borrelia burgdorferi*

| Derived from Protein | Amino Acid Sequence | SEQ ID NO |
|---|---|---|
| OspA | KVTSKDKSSTEEKFNEKGEVS | 10 |
| OspC | NSGKDGNTSANSADESVKGP | 11 |
| OspE | FILIGACKIHTSYDEQSSGESK | 12 |
| OspF | VQDLESSEQNVKKTEQEIKK | 13 |
| VlsE | FFVFINCKSQVADKDDPTNKFY | 14 |
| BmpA | DKSFNESALNGVKKVKEEFK | 15 |
| napA | SYIKKDDLDAIQLKLQELLASL | 16 |
| p41 | LSKTQEKLSSGYRINRASDDA | 17 |
| p100 | YKGPYDSTNTYEQIVGIGEFLAR | 18 |

To determine whether the antigenic peptides of *Borrelia* could be used in diagnostics we probed the sera of patients infected with *Borrelia*.

Previously we have observed that for diagnostic applications multiple peptides are better probes than single peptides. Hence, equal amounts of all the peptides of Table 2 were diluted (5 micrograms/ml in PBS) and coated on an ELISA plate (Nunc, MaxiSorp, ThermoFisher). The plates were incubated for 48 hours at 4° C. After washing, they were incubated with the sera of patients infected with *Borrelia* or healthy controls. These samples were further probed with anti-human horseradish peroxidase (HRP) and the data recorded after the addition of substrate.

Figure 2:
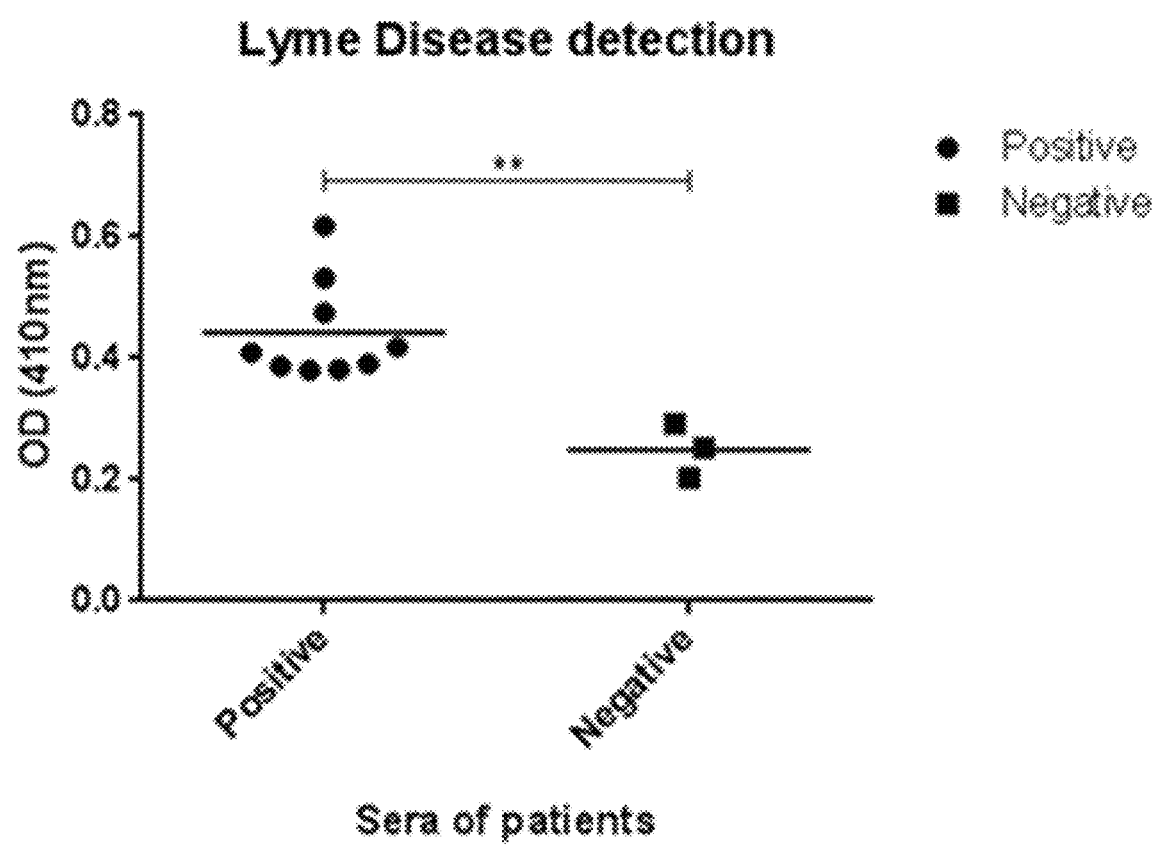
FIG. 2 is a graph showing the detection of *Borrelia* specific antibodies in blood samples (positive: (● known patients) (negative: ■ healthy controls).

From the results demonstrated in FIG. 2, the Lyme disease patient samples had higher values compared to the healthy controls. These ELISA data demonstrated that the peptides of Table 2 are useful in detecting anti-*B. burgdorferi* antibodies in infected subjects. Thus, these peptides are useful in a variety of diagnostic methods to detect Lyme Disease.

Example 3: Sonix Vaccine

In addition to peptide immunogens, we also used *Borrelia burgdorferi* to create a sonicated material useful as an immunogen (referred to as the "Sonix" vaccine). Previously, we demonstrated that sonicated Ehrlichia are antibody independent highly potent vaccine candidates. See, e.g., US Patent Publication No. 2016/0106825, incorporated by reference herein. The procedures for Ehrlichia as described were substantially used to create the *Borrelia* Sonix vaccine.

To create this vaccine composition, sonic waves were introduced into the liquid medium (e.g., PBS buffer) of a *Borrelia* bacterial sample at a frequency of about 20 to about 40 kHz. The minimum intensity (power) of the sonic waves was about 1 watt/cm$^2$ when utilizing a 20 kHz frequency. At this minimum level of power, cavitation is initiated. Preferably, the intensity level at about 20 kHz was 50 to 175 watts/cm$^2$.

In the case of *Borrelia*, the cavitation intensity and frequency was 20 kHz ranging from about 20 to about 150 watts/cm$^2$, or about 60-100 watts/cm$^2$. The samples were pulsed for about 30 seconds at the "hold" setting (about 25% of output of sonicator) and then rested for about 60 seconds in an ice bath. The sample was further sonicated for an additional 3 pulses (about 30 seconds). The duration of sonication may be several minutes or longer and most preferably is performed in at least three installments for about 30 seconds or longer. The sonication duration and intensity schedule resulted in maximum lysis and removal of any viable bacteria from the sonicate.

In certain aspects the sonication was conducted at room pressure and the sample maintained at a temperature of roughly about zero to 5° C. to avoid heating and to reduce the activity of cellular enzymes. After sonication of the bacteria the resulting product (Sonix vaccine) was directly available for use as a vaccine. No further additions or purification of the resulting material was necessary. The sonicated vaccine is suitable for injection as is, or for convenience of administration can be added to a pharmaceutically acceptable carrier or adjuvant.

Example 4: Protection Against Challenge with Lyme Disease (a) To determine whether the peptides of Table 2 could protect against *Borrelia* infection, we immunized C3H/HeN mice with 50 µg (each) of the peptides in the presence of the adjuvant (AddaVax) (0.2 ml) (subcutaneous immunization). The mice were immunized with two doses of the peptides two weeks apart. Two weeks after the second immunization, they were challenged with 10$^5$ *Borrelia* cells per mouse. Two weeks post-infection, mice were euthanized and tissues were collected to evaluate bacterial burden. Sera were isolated from the blood that was collected before and after bacterial challenge.

(b) We also sonicated *Borrelia burgdorferi* and used this material as an immunogen (referred to as the "Sonix" vaccine). We immunized C3H/HeN mice with about 50 micrograms of the Sonix vaccine in the presence of the adjuvant (AddaVax™) (0.2 ml) subcutaneously. An optional second dose is administered two weeks later. Two weeks after the second immunization, they were challenged with 10$^5$ *Borrelia* cells per mouse. Two weeks post-infection, mice were euthanized and tissues were collected to evaluate bacterial burden. Sera were isolated from the blood that was collected before and after bacterial challenge.

Figure 3:
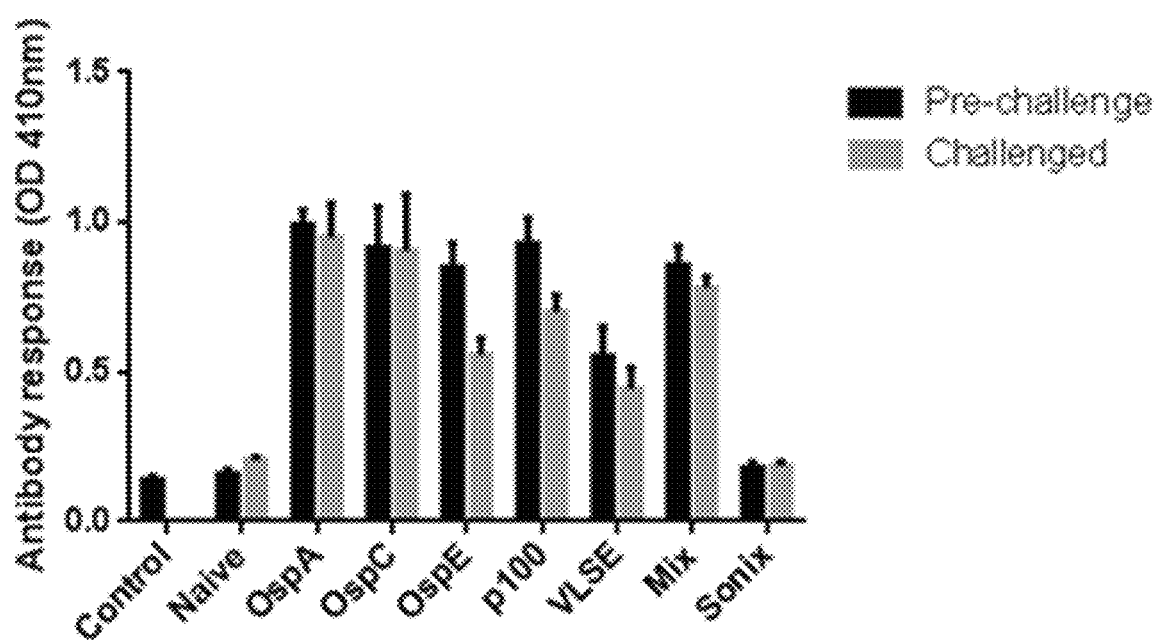
FIG. 3 is a graph showing that the antigenic peptides of *Borrelia* reacted with peptide-specific antibody before (dark bar) and after (light bar) challenge with the pathogen.

(c) Antibody Induction:

As illustrated in the results of FIG. 3, the peptides of the antigenic proteins of *Borrelia* reactivated with peptide-specific antibody before and after challenge with the pathogen. However, there was a decrease in antibody response after challenge irrespective of the peptides used. The Sonix vaccine did not induce any antibody after immunization or after challenge with the pathogen.

(d) Bacterial Load in Tissues After Vaccination

*Borrelia* is localized in the joints and heart tissues. The mouse tissues were collected after euthanization on day 14 after challenge and subjected to qPCR.

Figure 4:
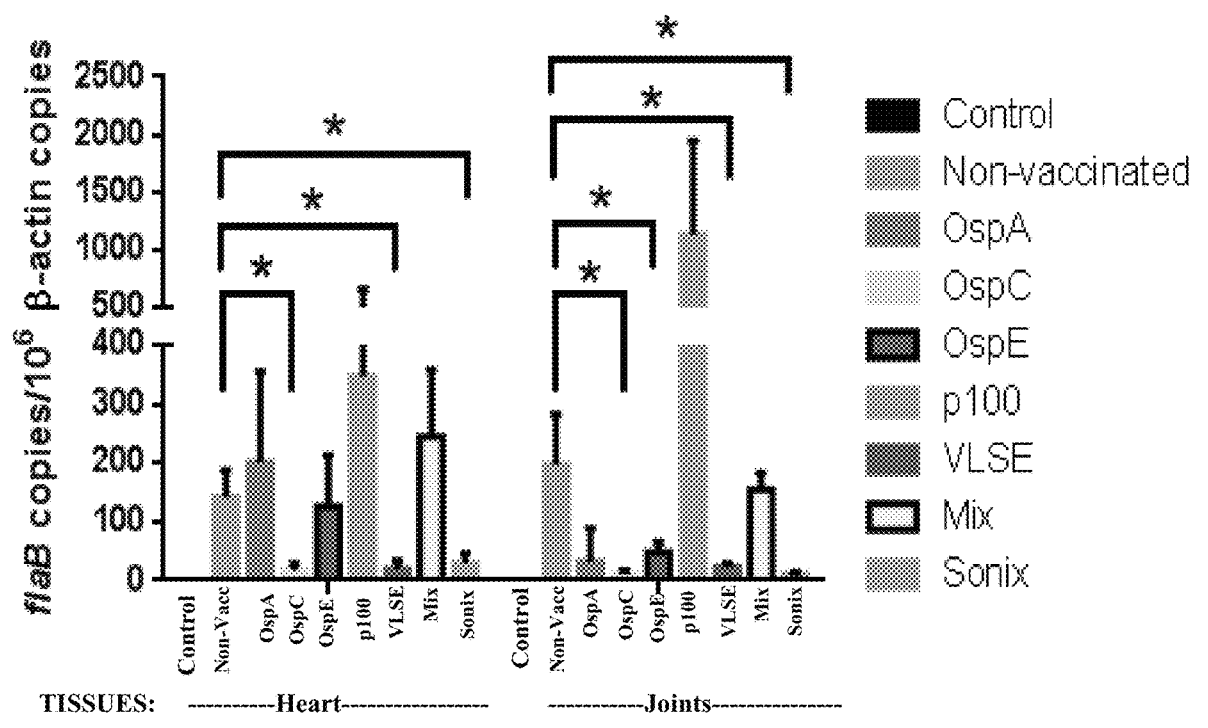

As demonstrated in the graph of FIG. 4, the naïve mice (unvaccinated) had the highest bacterial load in the heart and joint tissues. Mice immunized with OspC and VlsE had a significant reduction in the bacterial load in the heart and joint, demonstrating that the peptides provided protection against *Borrelia*.

Mice immunized with OspE had significantly lower levels of bacterial burden in the joint compared to the heart.

However, the peptide of p100 used in this test provided no significant protection against *Borrelia*.

The Sonix vaccine also provided protection against *Borrelia*. The heart and joint tissues had low copy number of the bacterial pathogen demonstrating that the Sonix vaccine is a highly potent vaccine candidate for Lyme disease.

These examples demonstrate that that compositions containing the identified *B. burgdorferi* peptides as well as the bacterial sonicate (Sonix) provide significant protection against the pathogenic *Borrelia* and are useful in vaccine compositions for Lyme disease (FIG. 4).

Each and every patent, patent application, and publication, including websites cited throughout specification are incorporated herein by reference. Similarly, the SEQ ID NOs which are referenced herein and which appear in the appended Sequence Listing are incorporated by reference. While the invention has been described with reference to particular embodiments, it will be appreciated that modifications can be made without departing from the spirit of the invention. Such modifications are intended to fall within the scope of the appended claims.

EMBODIMENTS

1. A reagent useful for the diagnosis of Lyme borreliosis in a subject comprising:
    (a) a peptide of SEQ ID NO: 10;
    (b) a peptide of SEQ ID NO: 11;
    (c) a peptide of SEQ ID NO: 12;
    (d) a peptide of SEQ ID NO: 13;
    (e) a peptide of SEQ ID NO: 14;
    (f) a peptide of SEQ ID NO: 15;
    (g) a peptide of SEQ ID NO: 16;
    (h) a peptide of SEQ ID NO: 17;
    (i) a peptide of SEQ ID NO: 18
    (j) a peptide having at least 90% identity to a peptide of any of SEQ ID NO: 10 to 18;
    (k) a peptide variant differing in one or more conservative amino acids to a peptide of any of SEQ ID NO: 10-18; or
    (l) a peptide variant differing in one or more naturally occurring amino acids from any of a peptide of SEQ ID NO: 10-18 based upon the strain of *B. burgdorferi* from which the peptide sequence is derived.

2. The reagent of embodiment 1, comprising a mixture of two or more peptides (a) through (l).

3. The reagent of embodiment 2, wherein said mixture comprises a combination of at least 3, 4, 5, 6, 7, 8, 9, 10 of said peptides (a)-(l).

4. The reaction of embodiment 1, comprising a combination of 2, 3, 4, 5, 6, 7, 8, or 9 of the peptides (a) through (i).

5. A reagent useful for the diagnosis of Lyme borreliosis in a subject comprising a nucleic acid sequence encoding:
    (a) a peptide of SEQ ID NO: 10;
    (b) a peptide of SEQ ID NO: 11;
    (c) a peptide of SEQ ID NO: 12;
    (d) a peptide of SEQ ID NO: 13;
    (e) a peptide of SEQ ID NO: 14;
    (f) a peptide of SEQ ID NO: 15;
    (g) a peptide of SEQ ID NO: 16;
    (h) a peptide of SEQ ID NO: 17;
    (i) a peptide of SEQ ID NO: 18
    (j) a peptide having at least 90% identity to a peptide of any of SEQ ID NO: 10 to 18;
    (k) a peptide variant differing in one or more conservative amino acids to a peptide of any of SEQ ID NO: 10-18; or
    (l) a peptide variant differing in one or more naturally occurring amino acids from any of a peptide of SEQ ID NO: 10-18 based upon the strain of *B. burgdorferi* from which the peptide sequence is derived.

6. The reagent of embodiment 5, comprising a mixture of nucleic acid sequences, each nucleic acid sequence encoding a different peptide (a) through (l).

7. The reagent of embodiment 6, wherein said mixture comprises at least 3, 4, 5, 6, 7, 8, 9, 10 of said nucleic acid sequences, each nucleic acid sequence encoding a different peptide (a) through (l).

8. The reagent of any of embodiments 1 or 4, wherein one or more of said peptides (a) to (l) or nucleic acid sequences encoding same is immobilized on an immobilization surface.

9. The reagent of any of embodiments 1 or 4, wherein one or more of said peptides or nucleic acid molecules is covalently or noncovalently joined to a molecule or moiety capable alone or in combination with one or more additional molecules of generating a detectable signal.

10. A method of diagnosing Lyme borreliosis in a subject, comprising contacting in vitro a biological sample from the subject in with a reagent of embodiments 1 or 4; and detecting in said sample the presence of an antibody that binds one or more of said peptides.

11. The method of embodiment 10, wherein the biological sample is whole blood, plasma, serum, ascites fluid, peritoneal fluid and a tissue or fluid from a tissue or joint sample.

12. A pharmaceutical composition for the treatment, retardation or prophylaxis of Lyme borreliosis comprising:
    (a) a peptide of SEQ ID NO: 10;
    (b) a peptide of SEQ ID NO: 11;
    (c) a peptide of SEQ ID NO: 12;
    (d) a peptide of SEQ ID NO: 13;
    (e) a peptide of SEQ ID NO: 14;
    (f) a peptide of SEQ ID NO: 15;
    (g) a peptide of SEQ ID NO: 16;
    (h) a peptide of SEQ ID NO: 17;
    (i) a peptide of SEQ ID NO: 18
    (j) a peptide having at least 90% identity to a peptide of any of SEQ ID NO: 10 to 18;
    (k) a peptide variant differing in one or more conservative amino acids to a peptide of any of SEQ ID NO: 10-18; or
    (l) a peptide variant differing in one or more naturally occurring amino acids from any of a peptide of SEQ ID NO: 10-18 based upon the strain of *B. burgdorferi* from which the peptide sequence is derived; or
    (m) a mixture of peptides selected from (a) through (l); and
    a pharmaceutically acceptable carrier, excipient or adjuvant.

13. The compositions of embodiment 12 comprising a mixture of peptides selected from (a) through (l).

14. A pharmaceutical composition for the treatment, retardation or prophylaxis of Lyme borreliosis comprising a nucleic acid sequence encoding
    (a) a peptide of SEQ ID NO: 10;
    (b) a peptide of SEQ ID NO: 11;
    (c) a peptide of SEQ ID NO: 12;
    (d) a peptide of SEQ ID NO: 13;
    (e) a peptide of SEQ ID NO: 14;
    (f) a peptide of SEQ ID NO: 15;
    (g) a peptide of SEQ ID NO: 16;

(h) a peptide of SEQ ID NO: 17;
(i) a peptide of SEQ ID NO: 18
(j) a peptide having at least 90% identity to a peptide of any of SEQ ID NO: 10 to 18;
(k) a peptide variant differing in one or more conservative amino acids to a peptide of any of SEQ ID NO: 10-18; or
(l) a peptide variant differing in one or more naturally occurring amino acids from any of a peptide of SEQ ID NO: 10-18 based upon the strain of *B. burgdorferi* from which the peptide sequence is derived; or
(m) a mixture of peptides selected from (a) through (l);
and a pharmaceutically acceptable carrier, excipient or adjuvant.

15. The composition of embodiment 14 comprising a mixture of nucleic acid sequences, each nucleic acid sequence encoding a different peptide (a) through (l).

16. A pharmaceutical composition for the treatment, retardation or prophylaxis of Lyme borreliosis comprising a sonicate of *Borrelia burgdorferi*.

17. The composition of embodiment 16, wherein the sonicate is present in an amount sufficient to elicit an antibody independent protective immune response.

18. A method of treating, preventing or retarding infection by comprising administering an effective amount of the pharmaceutical composition of embodiment 16 to a subject in need thereof, wherein said sonicate elicits an antibody-independent protective immune response.

The invention claimed is:

1. A reagent useful for the diagnosis of Lyme borreliosis in a subject comprising:
   i) a fusion protein of at least one outer surface protein consisting of:
      a) a peptide consisting of SEQ ID NO: 14;
      b) a peptide consisting of at least 90% identity to a peptide of SEQ ID NO: 14; or
      c) a peptide variant consisting of a sequence different in one or more conservative amino acids to a peptide of SEQ ID NO: 14; and
   ii) at least one additional outer surface protein of:
      (d) a peptide of SEQ ID NO: 10;
      (e) a peptide of SEQ ID NO: 11;
      (f) a peptide of SEQ ID NO: 12;
      (g) a peptide of SEQ ID NO: 13;
      (h) a peptide of SEQ ID NO: 14;
      (i) a peptide of SEQ ID NO: 15;
      (j) a peptide of SEQ ID NO: 16;
      (k) a peptide of SEQ ID NO: 17;
      (l) a peptide of SEQ ID NO: 18;
      (m) a peptide having at least 90% identity to a peptide of any of SEQ ID NO: 10 to 18; or
      (n) a peptide variant differing in one or more conservative amino acids to a peptide of any of SEQ ID NO: 10-18,
   wherein the at least one sequence of i) is not the same as the at least one sequence of ii).

2. The reagent of claim 1, wherein said fusion protein comprises a combination of at least 3, 4, 5, 6, 7, 8, 9, or 10 of said peptides (d)-(n).

3. A reagent useful for the diagnosis of Lyme borreliosis in a subject comprising at least two nucleic acid sequences that encode the fusion protein of claim 1.

4. The reagent of claim 3, wherein said fusion protein comprises at least 3, 4, 5, 6, 7, 8, 9, or 10 of said peptides (d)-(n).

5. The reagent of claim 1, wherein said peptides (a) to (n) are immobilized on an immobilization surface.

6. The reagent of claim 1, wherein said are covalently or noncovalently joined to a molecule or moiety capable alone or in combination with one or more additional molecules of generating a detectable signal.

7. The reagent of claim 1, wherein said composition comprises a fusion protein of 4 of said peptides (d)-(n).

8. A method of diagnosing Lyme borreliosis in a subject, comprising contacting in vitro a biological sample from the subject in with a reagent of claim 1; and detecting in said sample the presence of an antibody that binds one or more of said peptides.

9. The method of claim 8, wherein the biological sample is whole blood, plasma, serum, ascites fluid, peritoneal fluid or a tissue or fluid from a tissue or joint sample.

10. A pharmaceutical composition for the treatment, retardation, or prophylaxis of Lyme borreliosis comprising a pharmaceutically acceptable carrier, an excipient or adjuvant, and the reagent of claim 3.

11. The composition of claim 10, wherein said fusion protein comprises at least 3, 4, 5, 6, 7, 8, 9, or 10 of said peptides (d)-(n).

12. A pharmaceutical composition for the treatment, retardation, or prophylaxis of Lyme borreliosis comprising a pharmaceutically acceptable carrier, an excipient or adjuvant, and the reagent of claim 1.

13. The composition of claim 12, wherein said fusion protein comprises a combination of at least 3, 4, 5, 6, 7, 8, 9, or 10 of said peptides (d)-(n).

14. The composition of claim 12, wherein said peptides are covalently or noncovalently joined to a molecule or moiety capable alone or in combination with one or more additional molecules of generating a detectable signal.

15. The composition of claim 12, wherein said composition comprises a fusion protein of 4 of said peptides (d)-(n).

* * * * *

SEQUENCE LISTING

```
<160> NUMBER OF SEQ ID NOS: 18

<210> SEQ ID NO 1
<211> LENGTH: 273
<212> TYPE: PRT
<213> ORGANISM: Borrelia burgdorferi

<400> SEQUENCE: 1

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
                20                  25                  30

Asp Leu Pro Gly Glu Met Lys Val Leu Val Ser Lys Glu Lys Asn Lys
            35                  40                  45

Asp Gly Lys Tyr Asp Leu Ile Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
    115                 120                 125

Lys Gly Glu Val Ser Glu Lys Ile Ile Thr Arg Ala Asp Gly Thr Arg
130                 135                 140

Leu Glu Tyr Thr Gly Ile Lys Ser Asp Gly Ser Gly Lys Ala Lys Glu
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
    195                 200                 205

Ala Thr Lys Lys Thr Ala Ala Trp Asn Ser Gly Thr Ser Thr Leu Thr
210                 215                 220

Ile Thr Val Asn Ser Lys Lys Thr Lys Asp Leu Val Phe Thr Lys Glu
225                 230                 235                 240

Asn Thr Ile Thr Val Gln Gln Tyr Asp Ser Asn Gly Thr Lys Leu Glu
                245                 250                 255

Gly Ser Ala Val Glu Ile Thr Lys Leu Asp Glu Ile Lys Asn Ala Leu
            260                 265                 270
```

Lys

<210> SEQ ID NO 2
<211> LENGTH: 212
<212> TYPE: PRT
<213> ORGANISM: Borrelia burgdorferi

<400> SEQUENCE: 2

Met Lys Lys Asn Thr Leu Ser Ala Ile Leu Met Thr Leu Phe Leu Phe
1               5                   10                  15

Ile Ser Cys Asn Asn Ser Gly Lys Asp Gly Asn Thr Ser Ala Asn Ser
            20                  25                  30

Ala Asp Glu Ser Val Lys Gly Pro Asn Leu Thr Glu Ile Ser Lys Lys
        35                  40                  45

Ile Thr Glu Ser Asn Ala Val Val Leu Ala Val Lys Glu Val Glu Thr
    50                  55                  60

Leu Leu Ala Ser Ile Asp Glu Val Ala Lys Lys Ala Ile Gly Asn Leu
65                  70                  75                  80

Ile Ala Gln Asn Gly Leu Asn Ala Gly Ala Asn Gln Asn Gly Ser Leu
                85                  90                  95

Leu Ala Gly Ala Tyr Val Ile Ser Thr Leu Ile Ala Glu Lys Leu Asp
            100                 105                 110

Gly Leu Lys Asn Ser Glu Glu Leu Lys Glu Lys Ile Glu Asp Ala Lys
        115                 120                 125

Lys Cys Asn Lys Ala Phe Thr Asp Lys Leu Lys Ser Ser His Ala Glu
    130                 135                 140

Leu Gly Ile Ala Asn Gly Ala Ala Thr Asp Ala Asn Ala Lys Ala Ala
145                 150                 155                 160

Ile Leu Lys Thr Asn Gly Thr Lys Asp Lys Gly Ala Gln Glu Leu Glu
                165                 170                 175

Lys Leu Phe Glu Ser Val Lys Asn Leu Ser Lys Ala Ala Gln Glu Thr
            180                 185                 190

Leu Asn Asn Ser Val Lys Glu Leu Thr Ser Pro Val Val Ala Glu Ser
        195                 200                 205

Pro Lys Lys Pro
    210

<210> SEQ ID NO 3
<211> LENGTH: 171
<212> TYPE: PRT
<213> ORGANISM: Borrelia burgdorferi

<400> SEQUENCE: 3

Met Asn Lys Lys Met Lys Met Phe Ile Val Tyr Ala Val Phe Ile Leu
1               5                   10                  15

Ile Gly Ala Cys Lys Ile His Thr Ser Tyr Asp Glu Gln Ser Ser Gly
            20                  25                  30

Glu Ser Lys Val Lys Lys Ile Glu Phe Ser Lys Phe Thr Val Lys Ile
        35                  40                  45

Lys Asn Lys Asp Lys Ser Gly Asn Trp Thr Asp Leu Gly Asp Leu Val
    50                  55                  60

Val Arg Lys Glu Glu Asn Gly Ile Asp Thr Gly Leu Asn Ala Gly Gly
65                  70                  75                  80

His Ser Ala Thr Phe Phe Ser Leu Glu Glu Val Val Asn Asn Phe
                85                  90                  95

Val Lys Val Met Thr Glu Gly Gly Ser Phe Lys Thr Ser Leu Tyr Tyr

```
                    100                 105                 110
Gly Tyr Lys Glu Glu Gln Ser Val Ile Asn Gly Ile Gln Asn Lys Glu
            115                 120                 125

Ile Ile Thr Lys Ile Glu Lys Ile Asp Gly Thr Glu Tyr Ile Thr Phe
130                 135                 140

Ser Gly Asp Lys Ile Lys Asn Ser Gly Asp Lys Val Ala Glu Tyr Ala
145                 150                 155                 160

Ile Ser Leu Glu Glu Leu Lys Lys Asn Leu Lys
                165                 170

<210> SEQ ID NO 4
<211> LENGTH: 227
<212> TYPE: PRT
<213> ORGANISM: Borrelia burgdorferi

<400> SEQUENCE: 4

Met Asn Lys Lys Met Phe Ile Ile Cys Ala Val Phe Ala Leu Ile Ile
1               5                   10                  15

Ser Cys Lys Asn Tyr Ala Thr Ser Lys Asp Leu Glu Gly Ala Val Gln
            20                  25                  30

Asp Leu Glu Ser Ser Glu Gln Asn Val Lys Lys Thr Glu Gln Glu Ile
        35                  40                  45

Lys Lys Gln Val Glu Gly Phe Leu Glu Ile Leu Glu Thr Lys Asp Leu
50                  55                  60

Asn Lys Leu Asp Thr Lys Glu Ile Glu Lys Arg Ile Gln Glu Leu Lys
65                  70                  75                  80

Glu Lys Ile Glu Lys Leu Asp Ser Lys Lys Thr Ser Ile Glu Thr Tyr
                85                  90                  95

Ser Glu Tyr Glu Glu Lys Leu Lys Gln Ile Lys Glu Lys Leu Lys Gly
            100                 105                 110

Lys Ala Asp Leu Glu Asp Lys Leu Lys Gly Leu Glu Asp Ser Leu Lys
        115                 120                 125

Lys Lys Lys Glu Glu Arg Lys Lys Ala Leu Glu Asp Ala Lys Lys Lys
130                 135                 140

Phe Glu Glu Phe Lys Gly Gln Val Gly Ser Ala Thr Gly Val Thr Thr
145                 150                 155                 160

Gly His Arg Ala Gly Asn Gln Gly Ser Ile Gly Ala Gln Ala Trp Gln
                165                 170                 175

Cys Ala Asn Ser Leu Gly Leu Gly Val Ser Tyr Ser Ser Ser Thr Gly
            180                 185                 190

Thr Asp Ser Asn Glu Leu Ala Asn Lys Val Ile Asp Asp Ser Ile Lys
        195                 200                 205

Lys Ile Asp Glu Glu Leu Lys Asn Thr Ile Glu Asn Asn Gly Glu Val
210                 215                 220

Lys Lys Glu
225

<210> SEQ ID NO 5
<211> LENGTH: 357
<212> TYPE: PRT
<213> ORGANISM: Borrelia burgdorferi

<400> SEQUENCE: 5

Met Asn Thr Lys Lys Ile Ser Ser Ala Ile Leu Leu Thr Thr Phe Phe
1               5                   10                  15

Val Phe Ile Asn Cys Lys Ser Gln Val Ala Asp Lys Asp Asp Pro Thr
```

```
                 20                  25                  30
Asn Lys Phe Tyr Gln Ser Val Ile Gln Leu Gly Asn Gly Phe Leu Asp
             35                  40                  45

Val Phe Thr Ser Phe Gly Gly Leu Val Ala Glu Ala Phe Gly Phe Lys
 50                  55                  60

Ser Asp Pro Lys Lys Ser Asp Val Lys Thr Tyr Phe Thr Thr Val Ala
 65                  70                  75                  80

Ala Lys Leu Glu Lys Thr Lys Thr Asp Leu Asn Ser Leu Pro Lys Glu
                 85                  90                  95

Lys Ser Asp Ile Ser Ser Thr Thr Gly Lys Pro Asp Ser Thr Gly Ser
            100                 105                 110

Val Gly Thr Ala Val Glu Gly Ala Ile Lys Glu Val Ser Glu Leu Leu
            115                 120                 125

Asp Lys Leu Val Lys Ala Val Lys Thr Ala Glu Gly Ala Ser Ser Gly
130                 135                 140

Thr Ala Ala Ile Gly Glu Val Val Asp Asn Ala Ala Ala Ala Lys Ala
145                 150                 155                 160

Ala Asp Lys Asp Ser Val Thr Gly Ile Ala Lys Gly Ile Lys Glu Ile
                165                 170                 175

Val Glu Ala Ala Gly Gly Ser Lys Lys Leu Lys Ala Ala Ala Ala Lys
            180                 185                 190

Gly Glu Asn Asn Lys Gly Ala Gly Lys Leu Phe Gly Lys Ala Gly Asp
            195                 200                 205

Ala Ala His Gly Asp Ser Glu Ala Ala Ser Lys Ala Ala Gly Ala Val
            210                 215                 220

Ser Ala Val Ser Gly Glu Gln Ile Leu Ser Ala Ile Val Lys Ala Ala
225                 230                 235                 240

Ala Ala Gly Asp Gln Glu Gly Lys Lys Pro Gly Glu Ala Lys Asn Pro
                245                 250                 255

Ile Ala Ala Ala Ile Gly Glu Gly Asp Gly Asp Ala Glu Phe Asn Gln
            260                 265                 270

Asp Gly Met Lys Lys Asp Asp Gln Ile Ala Ala Ala Ile Ala Leu Arg
            275                 280                 285

Gly Met Ala Lys Asp Gly Lys Phe Ala Val Lys Asn Asp Glu Lys Gly
            290                 295                 300

Lys Ala Glu Gly Ala Ile Lys Gly Ala Ala Glu Ser Ala Val Arg Lys
305                 310                 315                 320

Val Leu Gly Ala Ile Thr Gly Leu Ile Gly Asp Ala Val Ser Ser Gly
                325                 330                 335

Leu Arg Lys Val Gly Asp Ser Val Lys Ala Ala Ser Lys Glu Thr Pro
            340                 345                 350

Pro Ala Leu Asn Lys
            355

<210> SEQ ID NO 6
<211> LENGTH: 178
<212> TYPE: PRT
<213> ORGANISM: Borrelia burgdorferi

<400> SEQUENCE: 6

Met Glu Lys Tyr Leu Ser Tyr Ile Lys Asp Asp Leu Asp Ala Ile
  1               5                  10                  15

Gln Leu Lys Leu Gln Glu Leu Leu Ala Ser Leu His Ile Phe Tyr Ser
             20                  25                  30
```

```
Asn Leu Arg Gly Ile His Trp Asn Ile Lys Asp Thr Asn Phe Phe Val
             35                   40                  45
Ile His Lys Lys Thr Gln Lys Leu Tyr Glu Tyr Ile Glu Lys Ile Ile
 50                  55                  60
Asp Ile Val Ala Glu Arg Ser Arg Met Leu Gly Tyr Asp Ser Glu Phe
 65                  70                  75                  80
Arg Tyr Ser Glu Phe Met Lys Lys Ser Phe Ile Lys Glu Leu Asp Ile
             85                  90                  95
Glu Ser Thr Ser Asn Phe Leu Pro Ser Met Gly Ser Ile Val Cys Ser
            100                 105                 110
Leu Thr Glu Ile Leu Lys Asn Ile Phe Gly Met Arg Lys Leu Ile Asp
            115                 120                 125
Thr Ala Gly Asp Tyr Gly Thr Ala Asn Ile Met Asp Asp Ile Met Ser
130                 135                 140
Asp Leu Glu Lys His Leu Trp Met His Lys Ala Leu Leu Glu Asn Cys
145                 150                 155                 160
Asp Cys Phe Cys His Asp Glu Asn Glu Ser Lys Cys Cys Glu Cys Asp
            165                 170                 175
Ala Lys

<210> SEQ ID NO 7
<211> LENGTH: 336
<212> TYPE: PRT
<213> ORGANISM: Borrelia burgdorferi

<400> SEQUENCE: 7

Met Ile Ile Asn His Asn Thr Ser Ala Ile Asn Ala Ser Arg Asn Asn
 1                   5                  10                  15
Ala Ile Asn Ala Ala Asn Leu Ser Lys Thr Gln Glu Lys Pro Ser Ser
             20                  25                  30
Gly Tyr Arg Ile Asn Arg Ala Ser Asp Asp Ala Ala Gly Met Gly Val
             35                  40                  45
Ser Gly Lys Ile Asn Ala Gln Ile Arg Gly Leu Ser Gln Ala Ser Arg
 50                  55                  60
Asn Thr Ser Lys Ala Ile Asn Phe Ile Gln Thr Thr Glu Gly Asn Leu
 65                  70                  75                  80
Asn Glu Val Glu Lys Val Leu Val Arg Met Lys Glu Leu Ala Val Gln
             85                  90                  95
Ser Gly Asn Gly Thr Tyr Ser Asp Ser Asp Arg Gly Ser Ile Gln Ile
            100                 105                 110
Glu Ile Glu Gln Leu Thr Asp Glu Ile Asn Arg Ile Ala Asp Gln Ala
            115                 120                 125
Gln Tyr Asn Gln Met His Met Leu Ser Asn Lys Ser Ala Ser Gln Asn
130                 135                 140
Val Lys Thr Ala Glu Glu Leu Gly Met Gln Pro Ala Lys Ile Asn Thr
145                 150                 155                 160
Pro Ala Ser Leu Ser Gly Ser Gln Ala Ser Trp Thr Leu Arg Val His
            165                 170                 175
Val Gly Ala Asn Gln Asp Glu Ala Ile Ala Val Asn Ile Tyr Ser Ala
            180                 185                 190
Asn Val Ala Asn Leu Phe Ala Gly Glu Gly Ala Gln Ala Ala Gln Ala
            195                 200                 205
Ala Pro Val Gln Glu Gly Ala Gln Glu Glu Gly Ala Gln Gln Pro Thr
210                 215                 220
```

```
Pro Ala Thr Ala Pro Ser Gln Gly Gly Val Asn Ser Pro Val Asn Val
225                 230                 235                 240

Thr Thr Thr Val Asp Ala Asn Thr Ser Leu Ala Lys Ile Glu Asn Ala
            245                 250                 255

Ile Arg Met Ile Ser Asp Gln Arg Ala Asn Leu Gly Ala Phe Gln Asn
            260                 265                 270

Arg Leu Glu Ser Ile Lys Asn Ser Thr Glu Tyr Ala Ile Glu Asn Leu
            275                 280                 285

Lys Ala Ser Tyr Ala Gln Ile Lys Asp Ala Thr Met Thr Asp Glu Val
            290                 295                 300

Val Ala Ala Thr Thr Lys Ser Ile Leu Thr Gln Ser Ala Met Ala Met
305                 310                 315                 320

Ile Ala Gln Ala Asn Gln Val Pro Gln Tyr Val Leu Ser Leu Leu Arg
            325                 330                 335
```

<210> SEQ ID NO 8
<211> LENGTH: 672
<212> TYPE: PRT
<213> ORGANISM: Borrelia burgdorferi

<400> SEQUENCE: 8

```
Met Lys Glu Leu Asp Lys Glu Lys Leu Arg Asp Phe Val Asn Met Asp
1               5                   10                  15

Leu Glu Phe Val Asn Tyr Lys Gly Pro Tyr Asp Ser Thr Asn Thr Tyr
            20                  25                  30

Glu Gln Ile Val Gly Ile Gly Glu Phe Leu Ala Arg Pro Leu Ile Asn
            35                  40                  45

Ser Asn Ser Asn Ser Ile Tyr Tyr Gly Lys Tyr Phe Ile Asn Arg Phe
50                  55                  60

Ile Asp Asp Gln Asp Lys Lys Ala Ser Val Asp Val Phe Ser Ile Gly
65                  70                  75                  80

Ser Arg Ser Gln Leu Asp Ser Ile Leu Asn Leu Arg Arg Ile Leu Thr
            85                  90                  95

Gly Tyr Leu Ile Lys Ser Phe Asp Tyr Glu Arg Ser Ser Ala Glu Leu
            100                 105                 110

Ile Ala Lys Val Ile Thr Ile His Asn Ala Val Tyr Arg Gly Asp Leu
            115                 120                 125

Asn Tyr Tyr Lys Glu Val Tyr Ile Glu Ala Ala Leu Lys Ser Leu Thr
            130                 135                 140

Lys Glu Asn Ala Gly Leu Ser Arg Val Tyr Ser Gln Trp Ala Gly Lys
145                 150                 155                 160

Thr Gln Ile Phe Ile Pro Leu Lys Lys Asn Ile Leu Ser Gly Lys Val
            165                 170                 175

Glu Ser Asp Ile Asp Ile Asp Ser Leu Val Thr Asp Lys Val Val Ala
            180                 185                 190

Ala Leu Leu Ser Glu Asn Glu Ala Gly Val Asn Phe Ala Arg Asp Ile
            195                 200                 205

Thr Asp Ile Gln Gly Glu Thr His Lys Ala Asp Gln Asp Lys Ile Asp
            210                 215                 220

Ile Glu Leu Asp Asn Val His Lys Ser Asp Ser Asn Ile Thr Glu Thr
225                 230                 235                 240

Ile Glu Asn Leu Arg Asp Gln Leu Glu Lys Ala Thr Asp Glu Glu His
            245                 250                 255

Arg Lys Glu Ile Glu Ser Gln Val Asp Ala Lys Lys Lys Gln Lys Glu
            260                 265                 270
```

Glu Leu Asp Lys Lys Ala Ile Asp Leu Asp Lys Ala Gln Gln Lys Leu
             275                 280                 285

Asp Ser Ser Glu Asp Asn Leu Asp Ile Gln Arg Asp Thr Val Arg Glu
     290                 295                 300

Lys Ile Gln Glu Asp Ile Asp Glu Ile Asn Lys Glu Lys Asn Leu Pro
305                 310                 315                 320

Lys Pro Gly Asp Val Ser Ser Pro Lys Val Asp Lys Gln Leu Gln Ile
                 325                 330                 335

Lys Glu Ser Leu Glu Asp Leu Gln Glu Gln Leu Lys Glu Thr Ser Asp
             340                 345                 350

Glu Asn Gln Lys Arg Glu Ile Glu Lys Gln Ile Glu Ile Lys Lys Ser
             355                 360                 365

Asp Glu Glu Leu Leu Lys Ser Lys Asp Pro Lys Ala Leu Asp Leu Asn
         370                 375                 380

Gly Asp Leu Asn Ser Lys Val Ser Ser Lys Glu Lys Ile Lys Gly Lys
385                 390                 395                 400

Glu Gly Glu Ile Val Lys Glu Ser Lys Ala Ser Leu Ala Asp Leu
                 405                 410                 415

Asn Asn Asp Glu Asn Leu Met Arg Pro Glu Asp Gln Lys Leu Ser Glu
             420                 425                 430

Asp Lys Lys Leu Asp Ser Lys Lys Asn Leu Lys Pro Val Ser Glu Ile
         435                 440                 445

Glu Arg Val Asn Glu Ile Ser Lys Ser Asn Asn Asn Glu Ile Ser Glu
     450                 455                 460

Ser Ser Pro Leu Tyr Lys Pro Ser Tyr Ser Asp Met Asp Ser Lys Glu
465                 470                 475                 480

Gly Ile Asp Asn Lys Asp Val Asn Leu Gln Glu Thr Lys Ser Gln Thr
                 485                 490                 495

Lys Ser Gln Pro Thr Ser Leu Asn Gln Asp Leu Thr Thr Met Ser Ile
             500                 505                 510

Asp Ser Ser Asn Pro Val Phe Leu Glu Val Ile Asp Pro Ile Thr Asn
         515                 520                 525

Leu Gly Thr Leu Gln Leu Ile Asp Leu Asn Thr Gly Val Arg Leu Lys
     530                 535                 540

Glu Ser Thr Gln Gln Gly Ile Gln Arg Tyr Gly Ile Tyr Glu Arg Glu
545                 550                 555                 560

Lys Asp Leu Val Val Ile Lys Met Asp Ser Gly Lys Ala Lys Leu Gln
                 565                 570                 575

Ile Leu Asn Lys Leu Glu Asn Leu Lys Val Ile Ser Glu Ser Asn Phe
             580                 585                 590

Glu Ile Asn Lys Asn Ser Ser Leu Tyr Val Asp Ser Lys Met Ile Leu
             595                 600                 605

Val Val Val Lys Asp Ser Gly Asn Val Trp Arg Leu Ala Lys Phe Ser
610                 615                 620

Pro Lys Asn Leu Asn Glu Phe Ile Leu Ser Glu Asn Lys Ile Leu Pro
625                 630                 635                 640

Phe Thr Ser Phe Ser Val Arg Lys Asn Phe Ile Tyr Leu Gln Asp Glu
                 645                 650                 655

Phe Lys Ser Leu Ile Thr Leu Asp Leu Asn Thr Leu Lys Lys Val Lys
             660                 665                 670

<210> SEQ ID NO 9
<211> LENGTH: 339

```
<212> TYPE: PRT
<213> ORGANISM: Borrelia burgdorferi

<400> SEQUENCE: 9

Met Asn Lys Ile Leu Leu Ile Leu Leu Glu Ser Ile Val Phe Leu
1               5                   10                  15

Ser Cys Ser Gly Lys Gly Ser Leu Gly Ser Glu Ile Pro Lys Val Ser
                20                  25                  30

Leu Ile Ile Asp Gly Thr Phe Asp Asp Lys Ser Phe Asn Glu Ser Ala
            35                  40                  45

Leu Asn Gly Val Lys Lys Val Lys Glu Glu Phe Lys Ile Glu Leu Val
50                  55                  60

Leu Lys Glu Ser Ser Ser Asn Ser Tyr Leu Ser Asp Leu Glu Gly Leu
65                  70                  75                  80

Lys Asp Ala Gly Ser Asp Leu Ile Trp Leu Ile Gly Tyr Arg Phe Ser
                85                  90                  95

Asp Val Ala Lys Val Ala Ala Leu Gln Asn Pro Asp Met Lys Tyr Ala
            100                 105                 110

Ile Ile Asp Pro Ile Tyr Ser Asn Asp Pro Ile Pro Ala Asn Leu Val
        115                 120                 125

Gly Met Thr Phe Arg Ala Gln Glu Gly Ala Phe Leu Thr Gly Tyr Ile
130                 135                 140

Ala Ala Arg Leu Ser Lys Thr Gly Lys Ile Gly Phe Leu Gly Gly Ile
145                 150                 155                 160

Glu Gly Glu Ile Val Asp Ala Phe Arg Tyr Gly Tyr Glu Ala Gly Ala
                165                 170                 175

Lys Tyr Ala Asn Lys Asp Ile Lys Ile Phe Thr Gln Tyr Ile Gly Ser
            180                 185                 190

Phe Ala Asp Leu Glu Ala Gly Arg Ser Val Ala Thr Arg Met Tyr Ser
        195                 200                 205

Asp Glu Ile Asp Ile Ile His His Ala Ala Gly Leu Gly Gly Ile Gly
210                 215                 220

Ala Ile Glu Val Ala Lys Glu Leu Gly Ser Gly His Tyr Ile Ile Gly
225                 230                 235                 240

Val Asp Glu Asp Gln Ala Tyr Leu Ala Pro Asp Asn Val Ile Thr Ser
                245                 250                 255

Thr Thr Lys Asp Val Gly Arg Ala Leu Asn Ile Phe Thr Ser Asn His
            260                 265                 270

Leu Lys Thr Asn Thr Phe Glu Gly Gly Lys Leu Ile Asn Tyr Gly Leu
        275                 280                 285

Lys Glu Gly Val Val Gly Phe Val Arg Asn Pro Lys Met Ile Ser Phe
290                 295                 300

Glu Leu Glu Lys Glu Ile Asp Asn Leu Ser Ser Lys Ile Ile Asn Lys
305                 310                 315                 320

Glu Ile Ile Val Pro Ser Asn Lys Glu Ser Tyr Glu Lys Phe Leu Lys
                325                 330                 335

Glu Phe Ile

<210> SEQ ID NO 10
<211> LENGTH: 21
<212> TYPE: PRT
<213> ORGANISM: Borrelia burgdorferi

<400> SEQUENCE: 10

Lys Val Thr Ser Lys Asp Lys Ser Ser Thr Glu Glu Lys Phe Asn Glu
```

```
1               5                   10                  15
Lys Gly Glu Val Ser
            20

<210> SEQ ID NO 11
<211> LENGTH: 20
<212> TYPE: PRT
<213> ORGANISM: Borrelia burgdorferi

<400> SEQUENCE: 11

Asn Ser Gly Lys Asp Gly Asn Thr Ser Ala Asn Ser Ala Asp Glu Ser
1               5                   10                  15

Val Lys Gly Pro
            20

<210> SEQ ID NO 12
<211> LENGTH: 22
<212> TYPE: PRT
<213> ORGANISM: Borrelia burgdorferi

<400> SEQUENCE: 12

Phe Ile Leu Ile Gly Ala Cys Lys Ile His Thr Ser Tyr Asp Glu Gln
1               5                   10                  15

Ser Ser Gly Glu Ser Lys
            20

<210> SEQ ID NO 13
<211> LENGTH: 20
<212> TYPE: PRT
<213> ORGANISM: Borrelia burgdorferi

<400> SEQUENCE: 13

Val Gln Asp Leu Glu Ser Ser Glu Gln Asn Val Lys Lys Thr Glu Gln
1               5                   10                  15

Glu Ile Lys Lys
            20

<210> SEQ ID NO 14
<211> LENGTH: 22
<212> TYPE: PRT
<213> ORGANISM: Borrelia burgdorferi

<400> SEQUENCE: 14

Phe Phe Val Phe Ile Asn Cys Lys Ser Gln Val Ala Asp Lys Asp Asp
1               5                   10                  15

Pro Thr Asn Lys Phe Tyr
            20

<210> SEQ ID NO 15
<211> LENGTH: 20
<212> TYPE: PRT
<213> ORGANISM: Borrelia burgdorferi

<400> SEQUENCE: 15

Asp Lys Ser Phe Asn Glu Ser Ala Leu Asn Gly Val Lys Lys Val Lys
1               5                   10                  15

Glu Glu Phe Lys
            20

<210> SEQ ID NO 16
<211> LENGTH: 22
<212> TYPE: PRT
```

```
<213> ORGANISM: Borrelia burgdorferi

<400> SEQUENCE: 16

Ser Tyr Ile Lys Lys Asp Asp Leu Asp Ala Ile Gln Leu Lys Leu Gln
1               5                   10                  15

Glu Leu Leu Ala Ser Leu
            20

<210> SEQ ID NO 17
<211> LENGTH: 21
<212> TYPE: PRT
<213> ORGANISM: Borrelia burgdorferi

<400> SEQUENCE: 17

Leu Ser Lys Thr Gln Glu Lys Leu Ser Ser Gly Tyr Arg Ile Asn Arg
1               5                   10                  15

Ala Ser Asp Asp Ala
            20

<210> SEQ ID NO 18
<211> LENGTH: 23
<212> TYPE: PRT
<213> ORGANISM: Borrelia burgdorferi

<400> SEQUENCE: 18

Tyr Lys Gly Pro Tyr Asp Ser Thr Asn Thr Tyr Glu Gln Ile Val Gly
1               5                   10                  15

Ile Gly Glu Phe Leu Ala Arg
            20
```